(12) United States Patent
Wang et al.

(10) Patent No.: US 7,238,525 B2
(45) Date of Patent: Jul. 3, 2007

(54) STRATEGY FOR LEUKEMIA THERAPY

(75) Inventors: Jean Y. J. Wang, San Diego, CA (US); Paolo Vigneri, Catania (IT)

(73) Assignee: The Regents of the University of California, Oakland, CA (US)

( * ) Notice: Subject to any disclaimer, the term of this patent is extended or adjusted under 35 U.S.C. 154(b) by 208 days.

(21) Appl. No.: 10/312,918

(22) PCT Filed: Jun. 29, 2001

(86) PCT No.: PCT/US01/20602

§ 371 (c)(1),
(2), (4) Date: Dec. 27, 2002

(87) PCT Pub. No.: WO02/00024

PCT Pub. Date: Jan. 3, 2002

(65) Prior Publication Data

US 2003/0162740 A1    Aug. 28, 2003

Related U.S. Application Data

(60) Provisional application No. 60/215,595, filed on Jun. 30, 2000.

(51) Int. Cl.
*C12N 5/08* (2006.01)
(52) U.S. Cl. .................. 435/375; 435/194; 435/372.1; 514/252.14; 514/252.18; 514/253.01
(58) Field of Classification Search ................ 514/224, 514/252.18, 86, 253.01, 252.14; 435/15, 435/194, 375, 372.1
See application file for complete search history.

(56) References Cited

OTHER PUBLICATIONS

Raanani et al. (Acta Haematol. 2005; 113 (3): 181-189).*
Gura (Science. 1997; 278: 1041-1042).*
Dan et al. (Cell Death Differ. Aug. 1998; 5 (8): 710-715).*
Nagar et al. (Cancer Res. Aug. 1, 2002; 62 (15): 4236-4243).*
Alefantis et al. (J. Biol. Chem. Jun. 13, 2003; 278 (24): 21814-21822).*
Kelland (Eur. J. Cancer. Apr. 2004; 40 (6): 827-836).*
Castro-Alcaraz (J. Immunol. 2002; 169: 3947-3953).*
Deininger et al. (Blood. Nov. 15, 2000; 96 (10): 3343-3356).*
Saijo et al. (Cancer Sci. Oct. 2004; 95 (10): 772-776).*
Ferrari et al. (Clin. Exp. Immunol. 2003; 132: 1-8).*
Pandha et al. (Current Opinion in Investigational Drugs 2000; 1 (1): 122-134).*
Amalfitano et al. (Current Gene Therapy 2002, 2: 111-133).*
Verma et al. (Nature 1997, 389: 239-242).*
Patterson AP. Memorandum (Jan. 14, 2003); pp. 3.*
Waller et al. (Anticancer Res. Mar.-Apr. 2000; 20 (2A): 809-814).*
Wang (Oncogene. Nov. 20, 2000; 19: 5643-5650).*
Huang et al. (Oncogene. 2002; 21: 8804-8816).*
Wiseniewski et al. (Cancer Res. Aug. 1, 2002; 62: 4244-4255).*
Beran, M. et al. Selective Inhibition of Cell Proliferation and BCR-ABL Phosphorylation in Acute Lymphoblastic Leukemia Cells Expressing M, 190,000 BCR-ABL Protein by a Tyrosine Kinase Inhibitor (CGP-57148). Clinical Cancer Research, vol. 4, 1998, 1661-1672.
Cornetta, K. et al. Retroviral mediated gene transfer in chronic myelogenous leukaemia. British Journal of Haematology, 87, 1994, 308-316.
Deininger, M. et al. The Tyrosine Kinase Inhibitor CGP57148B Selectively Inhibits the Growth of BCR-ABL-Positive Cells. Blood, vol. 90, No. 9, 1997, 3691-3698.
Dorsey, J. et al. The Pyrido[2,3-*d*]pyrimidine Derivative PD180970 Inhibits $p210^{Bcr-Abl}$ Tyrosine Kinase and Induces Apoptosis of K562 Leukemia Cells. Cancer Research 60, 2000, 3127-3131.
Issaad, C. et al. Retro virus-mediated BCR-ABL (P210) gene transfer into the pluripotent human hematopoietic cell line UT-7 induces growth factor-independence and erythroid differentiation-bcr-abl oncogene gene transfer results in growth factor independence and erythroid differentiation; application in antisense gene transfer and cancer therapy (abstract). Blood, 84, 10, suppl. 1, 138a, 1994, 537.
Komiyama, K. et al. Antitumor Activity of Leptomycin B. The Journal of Antibiotics, vol. XXXVIII, No. 3, 1985, 427-429.
Marley, S. et al. The tyrosine kinase inhibitor ST1571, like interferon-α, preferentially reduces the capacity for amplification of granulocyte-macrophage progenitors from patients with chronic myeloid leukemia. Experimental Hematology, 28, 2000, 551-557.
Melo, J. Inviting leukemic cells to waltz with the devil. Nature Medicine. vol. 7, No. 2, 2001, 156-157.
Smart, P. et al. Effects on normal fibroblasts and neuroblastoma cells of the activation of the p53 response by the nuclear export inhibitor leptomycin B. Oncogene, 18, 1999, 7378-7386.
Vigneri, P. et al. Induction of apoptosis in chronic myelogenous leukemia cells through nuclear entrapment of BCR-ABL tyrosine kinase. Nature Medicine, vol. 7, No. 2, 2001, 228-234.
Waller, C. et al. Growth Inhibition of $Ph^+$ Progenitor Cells from CML Patients Using the Tyrosine Kinase Inhibitor CGP57148B. Anticancer Research, 20, 2000, 809-814.

* cited by examiner

*Primary Examiner*—Stephen L. Rawlings
(74) *Attorney, Agent, or Firm*—Biotactica, LLC

(57) ABSTRACT

The chimeric Bcr-Abl oncoprotein is the molecular hallmark of chronic myelogenous leukemia (CML). In the cytoplasm, the protein transduces a growth signal that is responsible for overexpansion of cells. In the nucleus, the protein induces apoptosis. The invention is a method of treating cancer/killing Bcr-Abl expressing cells by inducing the translocation of Bcr-Abl to the nucleus to activate the apoptotic pathway in cancer cells.

6 Claims, 3 Drawing Sheets

FIGURE 1. Selected small-molecule ATP-competitive protein kinase inhibitors in development

| Target Kinase[A] | Company | Name | Clinical Phase |
|---|---|---|---|
| Bcr-Abl | Novartis | CGP 57148B (STI571) | Phase I/II |
| CDKs | Hoechst Marion Roussel | (L86-8275, NSC-649890) | Phase I |
| EGF-R | Boehringer-Ingelheim | BIBX 1382 | Phase I |
| EGF-R | Novartis | PKI 116 | Phase I |
| EGF-R | Pfizer/OSI Pharmaceuticals | CP358,774 | Phase II |
| EGF-R | Warner-Lambert | PD 0183805 | Phase I |
| EGF-R | Zeneca | ZD 1839 | Phase II |
| PKC/Trk[B] | Cephalon/Kyowa Hakko | CEP 2563<br>CEP 701 | Phase I |
| PKC[B] | Kyowa Hakko | UNC-01 | Phase I/II |
| PKCβ | Lilly | LY-333531 | Phase III |
| PKC[B] | Novartis | CGP 41251 (STI 412) | Phase I/II |
| PDGF-Rβ | Sugen | SU 6668 | Phase I |
| VEGF-R | Novartis/Schering | CGP 79787 (PTK787/ZK22584) | Phase I |
| VEGF-R | Pfizer/OSI Pharmaceuticals | CP-564,959 | PCD |
| VEGF-R | Sugen | SU 5416 | Phase I |
| VEGF-R | Zeneca | ZD4910 | PCD |

[A] Protein kinase targeted. A number of these molecules are broad-spectrum kinase inhibitors [B] Staurosporine class represents examples of broad spectrum kinase inhibitors. PCD, preclinical development. These compounds may have progressed to phase I clinical trials. Table from Drucker and Lydon, 2000.

Figure 2. Nuclear localization of active Bcr-Abl kinase kills cells

| Protein | Treatment | % TUNEL Positive Cells | |
|---|---|---|---|
| | | Transfected cells | Untransfected cells |
| Bcr-Abl | none | 0 | 0 |
| Bcr-Abl | LMB + STI571 | 23 | 10 |
| Bcr-Abl | LMB + STI571 => media | 77 | 13 |
| Bcr-Abl-NES | none | 0 | 3 |
| Bcr-Abl-NES | STI571 => media | 60 | 3 |
| Bcr-Abl-KD | none | 0 | 0 |
| Bcr-Abl-KD | LMB | 10 | 7 |

The indicated Bcr-Abl proteins were expressed in COS-1 cells by transient transfection using the calcium phosphate method. After transfection, cells were left untreated (none) or exposed to the indicated drug regimens as described in Example 4. => indicates extensive washing. Cell death was scored by TUNEL assay. Transfected and untransfected cells on the same coverslip were scored. Numbers represent percent of TUNEL positive cells out of 30 cells counted from a representative experiment.

SEQUENCE LISTING

<160> NUMBER OF SEQ ID NOS: 4

<210> SEQ ID NO 1
<211> LENGTH: 4705
<212> TYPE: DNA
<213> ORGANISM: Homo sapien/ Mus musculus
<220> FEATURE:
<221> NAME/KEY: CDS
<222> LOCATION: (1)..(4704)
<223> OTHER INFORMATION:

<400> SEQUENCE: 1

```
atg gtg gac ccg gtg ggc ttc gcg gag gcg tgg aag gcg cag ttc ccg      48
Met Val Asp Pro Val Gly Phe Ala Glu Ala Trp Lys Ala Gln Phe Pro
1               5                   10                  15 gac tca gag ccc ccg cgc atg gag ctg cgc tca gtg ggc gac atc gag      96
Asp Ser Glu Pro Pro Arg Met Glu Leu Arg Ser Val Gly Asp Ile Glu
            20                  25                  30 cag gag ctg gag cgc tgc aag gcc tcc att cgg cgc ctg gag cag gag     144
Gln Glu Leu Glu Arg Cys Lys Ala Ser Ile Arg Arg Leu Glu Gln Glu
        35                  40                  45 gtg aac cag gag cgc ttc cgc atg atc tac ctg cag acg ttg ctg gcc     192
Val Asn Gln Glu Arg Phe Arg Met Ile Tyr Leu Gln Thr Leu Leu Ala
    50                  55                  60 aag gaa aag aag agc tat gac cgg cag cga tgg ggc ttc cgg cgc gcg     240
Lys Glu Lys Lys Ser Tyr Asp Arg Gln Arg Trp Gly Phe Arg Arg Ala
65              70                  75                  80 gcg cag gcc ccc gac ggc gcc tcc gag ccc cga gcg tcc gcg tcg cgc     288
Ala Gln Ala Pro Asp Gly Ala Ser Glu Pro Arg Ala Ser Ala Ser Arg
                85                  90                  95 ccg cag cca gcg ccc gcc gac gga gcc gac ccg ccg ccc gcc gag gag     336
Pro Gln Pro Ala Pro Ala Asp Gly Ala Asp Pro Pro Pro Ala Glu Glu
            100                 105                 110 ccc gag gcc cgg ccc gac ggc gag ggt tct ccg ggt aag gcc agg ccc     384
Pro Glu Ala Arg Pro Asp Gly Glu Gly Ser Pro Gly Lys Ala Arg Pro
        115                 120                 125 ggg acc gcc cgc agg ccc ggg gca gcc gcg tcg ggg gaa cgg gac gac     432
Gly Thr Ala Arg Arg Pro Gly Ala Ala Ala Ser Gly Glu Arg Asp Asp
    130                 135                 140 cgg gga ccc ccc gcc agc gtg gcg gcg ctc agg tcc aac ttc gag cgg     480
Arg Gly Pro Pro Ala Ser Val Ala Ala Leu Arg Ser Asn Phe Glu Arg
145                 150                 155                 160 atc cgg aag ggc cat ggc cag ccc ggg gcg gac gcc gag aag ccc ttc     528
Ile Arg Lys Gly His Gly Gln Pro Gly Ala Asp Ala Glu Lys Pro Phe
                165                 170                 175 tac gtg aac gtc gag ttt cac cac gag cgc ggc ctg gtg aag gtc aac     576
Tyr Val Asn Val Glu Phe His His Glu Arg Gly Leu Val Lys Val Asn
            180                 185                 190 gac aaa gag gtg tcg gac cgc atc agc tcc ctt ggc agc cag gcc atg     624
Asp Lys Glu Val Ser Asp Arg Ile Ser Ser Leu Gly Ser Gln Ala Met
        195                 200                 205 cag atg gag cgc aaa aag tcc cag cac ggc gcg ggc tcg agc gtg ggg     672
Gln Met Glu Arg Lys Lys Ser Gln His Gly Ala Gly Ser Ser Val Gly
    210                 215                 220 gat gca tcc agg ccc cct tac cgg gga cgc tcc tcg gag agc agc tgc     720
Asp Ala Ser Arg Pro Pro Tyr Arg Gly Arg Ser Ser Glu Ser Ser Cys
225                 230                 235                 240 ggc gtc gac ggc gac tac gag gac gcc gag ttg aac ccc cgc ttc ctg     768
Gly Val Asp Gly Asp Tyr Glu Asp Ala Glu Leu Asn Pro Arg Phe Leu
                245                 250                 255 aag gac aac ctg atc gac gcc aat ggc ggt agc agg ccc cct tgg ccg     816
Lys Asp Asn Leu Ile Asp Ala Asn Gly Gly Ser Arg Pro Pro Trp Pro
            260                 265                 270 ccc ctg gag tac cag ccc tac cag agc atc tac gtc ggg ggc atc atg     864
Pro Leu Glu Tyr Gln Pro Tyr Gln Ser Ile Tyr Val Gly Gly Ile Met
        275                 280                 285 gaa ggg gag ggc aag ggc ccg ctc ctg cgc agc cag agc acc tct gag     912
Glu Gly Glu Gly Lys Gly Pro Leu Leu Arg Ser Gln Ser Thr Ser Glu
    290                 295                 300 cag gag aag cgc ctt acc tgg ccc cgc agg tcc tac tcc ccc cgg agt     960
```

```
Gln Glu Lys Arg Leu Thr Trp Pro Arg Arg Ser Tyr Ser Pro Arg Ser
305                 310                 315                 320 ttt gag gat tgc gga ggc ggc tat acc ccg gac tgc agc tcc aat gag    1008
Phe Glu Asp Cys Gly Gly Gly Tyr Thr Pro Asp Cys Ser Ser Asn Glu
                325                 330                 335 aac ctc acc tcc agc gag gag gac ttc tcc tct ggc cag tcc agc cgc    1056
Asn Leu Thr Ser Ser Glu Glu Asp Phe Ser Ser Gly Gln Ser Ser Arg
            340                 345                 350 gtg tcc cca agc ccc acc acc tac cgc atg ttc cgg gac aaa agc cgc    1104
Val Ser Pro Ser Pro Thr Thr Tyr Arg Met Phe Arg Asp Lys Ser Arg
        355                 360                 365 tct ccc tcg cag aac tcg caa cag tcc ttc gac agc agc agt ccc ccc    1152
Ser Pro Ser Gln Asn Ser Gln Gln Ser Phe Asp Ser Ser Ser Pro Pro
    370                 375                 380 acg ccg cag tgc cat aag cgg cac cgg cac tgc ccg gtt gtc gtg tcc    1200
Thr Pro Gln Cys His Lys Arg His Arg His Cys Pro Val Val Val Ser
385                 390                 395                 400 gag gcc acc atc gtg ggc gtc cgc aag acc ggg cag atc tgg ccc aac    1248
Glu Ala Thr Ile Val Gly Val Arg Lys Thr Gly Gln Ile Trp Pro Asn
                405                 410                 415 gat gac gag ggc gcc ttc cat gga gac gca gat ggc tcg ttc gga aca    1296
Asp Asp Glu Gly Ala Phe His Gly Asp Ala Asp Gly Ser Phe Gly Thr
            420                 425                 430 cca cct gga tac ggc tgc gct gca gac cgg gca gag gag cag cgc cgg    1344
Pro Pro Gly Tyr Gly Cys Ala Ala Asp Arg Ala Glu Glu Gln Arg Arg
        435                 440                 445 cac caa gat ggg ctg ccc tac att gat gac tcg ccc tcc tca tcg ccc    1392
His Gln Asp Gly Leu Pro Tyr Ile Asp Asp Ser Pro Ser Ser Ser Pro
    450                 455                 460 cac ctc agc agc aag ggc agg ggc agc cgg gat gcg ctg gtc tcg gga    1440
His Leu Ser Ser Lys Gly Arg Gly Ser Arg Asp Ala Leu Val Ser Gly
465                 470                 475                 480 gcc ctg aag tcc act aaa gcg agt gag ctg gac ttg gaa aag ggc ttg    1488
Ala Leu Lys Ser Thr Lys Ala Ser Glu Leu Asp Leu Glu Lys Gly Leu
                485                 490                 495 gag atg aga aaa tgg gtc ctg tcg gga atc ctg gct agc ggt acc gaa    1536
Glu Met Arg Lys Trp Val Leu Ser Gly Ile Leu Ala Ser Gly Thr Glu
            500                 505                 510 aag ctc cgg gtc ttg ggt tat aat cac aat ggg gaa tgg tgt gaa gcc    1584
Lys Leu Arg Val Leu Gly Tyr Asn His Asn Gly Glu Trp Cys Glu Ala
        515                 520                 525 caa acg aaa aat ggc caa gga tgg gtc cca agc aac tac atc acc ccc    1632
Gln Thr Lys Asn Gly Gln Gly Trp Val Pro Ser Asn Tyr Ile Thr Pro
    530                 535                 540 gtc aac agc ctg gag aaa cat tcc tgg tat cat ggc cct gta tct cgg    1680
Val Asn Ser Leu Glu Lys His Ser Trp Tyr His Gly Pro Val Ser Arg
545                 550                 555                 560 aat gct gct gag tat ctg ctg agc agc gga atc aac ggc agc ttc tta    1728
Asn Ala Ala Glu Tyr Leu Leu Ser Ser Gly Ile Asn Gly Ser Phe Leu
                565                 570                 575 gtg cgg gag agt gag agt agc cct ggc cag aga tcc atc tcg ctg cgg    1776
Val Arg Glu Ser Glu Ser Ser Pro Gly Gln Arg Ser Ile Ser Leu Arg
            580                 585                 590 tat gaa ggg agg gtg tac cac tac agg atc aac act gcc tct gat ggc    1824
Tyr Glu Gly Arg Val Tyr His Tyr Arg Ile Asn Thr Ala Ser Asp Gly
        595                 600                 605 aag ctg tac gtg tcc tcc gag agc cgc ttc aac act ctg gct gag tta    1872
Lys Leu Tyr Val Ser Ser Glu Ser Arg Phe Asn Thr Leu Ala Glu Leu
    610                 615                 620
```

-continued

| | | |
|---|---|---|
| gtt cac cat cac tcc acg gtg gct gat ggc ctc atc acc aca ctc cac<br>Val His His His Ser Thr Val Ala Asp Gly Leu Ile Thr Thr Leu His<br>625                               630                        635                      640 | 1920 |
| tac cca gct ccc aag cgc aac aag ccc act atc tac ggt gtg tcc ccc<br>Tyr Pro Ala Pro Lys Arg Asn Lys Pro Thr Ile Tyr Gly Val Ser Pro<br>                      645                        650                      655 | 1968 |
| aac tac gac aag tgg gaa atg gag cgc acc gac atc acc atg aag cac<br>Asn Tyr Asp Lys Trp Glu Met Glu Arg Thr Asp Ile Thr Met Lys His<br>               660                   665                    670 | 2016 |
| aag ttg ggt gga ggc cag tac ggg gag gtg tac gag ggc gtt tgg aag<br>Lys Leu Gly Gly Gly Gln Tyr Gly Glu Val Tyr Glu Gly Val Trp Lys<br>        675                        680                        685 | 2064 |
| aag tac agc ctc act gtg gcc gtg aag acc ttg aag gag gac acc atg<br>Lys Tyr Ser Leu Thr Val Ala Val Lys Thr Leu Lys Glu Asp Thr Met<br>690                               695                        700 | 2112 |
| gag gtg gag gag ttc ctg aag gaa gcg gcg gtg atg aag gag atc aaa<br>Glu Val Glu Glu Phe Leu Lys Glu Ala Ala Val Met Lys Glu Ile Lys<br>705                               710                        715                    720 | 2160 |
| cac cct aac ctg gtg cag ctg cta ggg gtg tgt acc cgg gaa cca cca<br>His Pro Asn Leu Val Gln Leu Leu Gly Val Cys Thr Arg Glu Pro Pro<br>                          725                        730                    735 | 2208 |
| ttc tac ata atc act gag ttc atg acc tat ggg aac ctg ctg gac tac<br>Phe Tyr Ile Ile Thr Glu Phe Met Thr Tyr Gly Asn Leu Leu Asp Tyr<br>                    740                        745                    750 | 2256 |
| ctg agg gag tgt aac cgg cag gag gtg agc gcc gtg gta ctg ctc tac<br>Leu Arg Glu Cys Asn Arg Gln Glu Val Ser Ala Val Val Leu Leu Tyr<br>        755                        760                        765 | 2304 |
| atg gcc aca cag atc tca tca gcc atg gag tac ttg gag aag aag aac<br>Met Ala Thr Gln Ile Ser Ser Ala Met Glu Tyr Leu Glu Lys Lys Asn<br>770                               775                        780 | 2352 |
| ttc atc cac aga gac ctt gct gcc cgg aac tgc ctg gta ggg gaa aac<br>Phe Ile His Arg Asp Leu Ala Ala Arg Asn Cys Leu Val Gly Glu Asn<br>785                               790                        795                    800 | 2400 |
| cac ttg gtg aag gtg gct gat ttt ggc ctg agc agg ttg atg aca ggg<br>His Leu Val Lys Val Ala Asp Phe Gly Leu Ser Arg Leu Met Thr Gly<br>                        805                        810                    815 | 2448 |
| gac acc tac acg gcc cat gct gga gcc aaa ttc ccc atc aaa tgg acc<br>Asp Thr Tyr Thr Ala His Ala Gly Ala Lys Phe Pro Ile Lys Trp Thr<br>               820                   825                    830 | 2496 |
| gca cct gag agc ctg gcc tac aac aag ttc tcc atc aag tcg gac gtg<br>Ala Pro Glu Ser Leu Ala Tyr Asn Lys Phe Ser Ile Lys Ser Asp Val<br>        835                        840                        845 | 2544 |
| tgg gca ttt gga gta ttg ctc tgg gag att gct acc tat ggc atg tca<br>Trp Ala Phe Gly Val Leu Leu Trp Glu Ile Ala Thr Tyr Gly Met Ser<br>850                               855                        860 | 2592 |
| cct tac ccg gga att gac ctg tct cag gtt tat gag ctg ctg gaa aaa<br>Pro Tyr Pro Gly Ile Asp Leu Ser Gln Val Tyr Glu Leu Leu Glu Lys<br>865                               870                        875                    880 | 2640 |
| gac tac cgc atg gag cgc cct gaa ggc tgc ccg gag aag gtc tac gag<br>Asp Tyr Arg Met Glu Arg Pro Glu Gly Cys Pro Glu Lys Val Tyr Glu<br>                        885                        890                    895 | 2688 |
| ctc atg cga gca tgt tgg cag tgg aac ccc tct gac cgg ccc tcc ttt<br>Leu Met Arg Ala Cys Trp Gln Trp Asn Pro Ser Asp Arg Pro Ser Phe<br>               900                   905                    910 | 2736 |
| gct gaa atc cac caa gcc ttt gaa acc atg ttc cag gaa tcc agt atc<br>Ala Glu Ile His Gln Ala Phe Glu Thr Met Phe Gln Glu Ser Ser Ile<br>        915                        920                        925 | 2784 |
| tca gat gag gtg gag aag gag ctg ggg aaa cga ggc acg aga gga ggt<br>Ser Asp Glu Val Glu Lys Glu Leu Gly Lys Arg Gly Thr Arg Gly Gly<br>930                               935                        940 | 2832 |

-continued

| | |
|---|---|
| gct ggg agt atg ctg cag gcc cca gag ctg ccc acc aag acc aga acc<br>Ala Gly Ser Met Leu Gln Ala Pro Glu Leu Pro Thr Lys Thr Arg Thr<br>945                  950                  955                  960 | 2880 |
| tgc agg aga gca gct gag cag aaa gat gcg cct gac acc cct gag ctg<br>Cys Arg Arg Ala Ala Glu Gln Lys Asp Ala Pro Asp Thr Pro Glu Leu<br>                965                  970                  975 | 2928 |
| ctc cac acg aag ggc ctg gga gaa agc gat gca ctg gac agt gag cct<br>Leu His Thr Lys Gly Leu Gly Glu Ser Asp Ala Leu Asp Ser Glu Pro<br>        980                  985                  990 | 2976 |
| gct gta tcg cca ctg ctt cct cgg aaa gag cgc ggg ccc cca gac ggc<br>Ala Val Ser Pro Leu Leu Pro Arg Lys Glu Arg Gly Pro Pro Asp Gly<br>          995                  1000              1005 | 3024 |
| agc cta aat gaa gat gag cgc ctt ctc ccc aga gac aga aag acc<br>Ser Leu Asn Glu Asp Glu Arg Leu Leu Pro Arg Asp Arg Lys Thr<br>        1010                  1015              1020 | 3069 |
| aac ctg ttc agc gct ttg atc aag aag aag aag aaa atg gcg ccg<br>Asn Leu Phe Ser Ala Leu Ile Lys Lys Lys Lys Lys Met Ala Pro<br>        1025                  1030              1035 | 3114 |
| acg ccc cct aag cgc agc agt tcc ttc cga gag atg gat ggc cag<br>Thr Pro Pro Lys Arg Ser Ser Phe Arg Glu Met Asp Gly Gln<br>        1040                  1045              1050 | 3159 |
| cca gac cgc aga ggg gct agt gag gat gac agc agg gaa ctc tgc<br>Pro Asp Arg Arg Gly Ala Ser Glu Asp Asp Ser Arg Glu Leu Cys<br>        1055                  1060              1065 | 3204 |
| aat gga cca cca gct ctc acc tca gac gca gca gag cct acc aag<br>Asn Gly Pro Pro Ala Leu Thr Ser Asp Ala Ala Glu Pro Thr Lys<br>        1070                  1075              1080 | 3249 |
| tcc cca aag gcc agc aat ggg gct ggc gtc cct aat gga gcc ttc<br>Ser Pro Lys Ala Ser Asn Gly Ala Gly Val Pro Asn Gly Ala Phe<br>        1085                  1090              1095 | 3294 |
| cgg gag ccg ggc aac tca ggc ttc cgt tct ccc cac atg tgg aaa<br>Arg Glu Pro Gly Asn Ser Gly Phe Arg Ser Pro His Met Trp Lys<br>        1100                  1105              1110 | 3339 |
| aag tcc agc aca ctg acc ggg agc cgc ctg gct gct gcc gaa gag<br>Lys Ser Ser Thr Leu Thr Gly Ser Arg Leu Ala Ala Ala Glu Glu<br>        1115                  1120              1125 | 3384 |
| gag agc ggc atg agc tcc agt aag cgc ttc ctg cgt tct tgt tcg<br>Glu Ser Gly Met Ser Ser Ser Lys Arg Phe Leu Arg Ser Cys Ser<br>        1130                  1135              1140 | 3429 |
| gcc tcc tgc atg ccc cat ggg gca agg gac aca gag tgg cgg tcg<br>Ala Ser Cys Met Pro His Gly Ala Arg Asp Thr Glu Trp Arg Ser<br>        1145                  1150              1155 | 3474 |
| gtc acg ctg cct cga gac ctg ccg tct gct ggc aag cag ttt gac<br>Val Thr Leu Pro Arg Asp Leu Pro Ser Ala Gly Lys Gln Phe Asp<br>        1160                  1165              1170 | 3519 |
| tca tcc acc ttt gga ggg cac aaa agc gaa aag cca gct ctg cct<br>Ser Ser Thr Phe Gly Gly His Lys Ser Glu Lys Pro Ala Leu Pro<br>        1175                  1180              1185 | 3564 |
| cgg aaa cgc acc agt gag agc agg tct gag cag gtg gcc aaa agc<br>Arg Lys Arg Thr Ser Glu Ser Arg Ser Glu Gln Val Ala Lys Ser<br>        1190                  1195              1200 | 3609 |
| acg gcg atg ccc ctc ccc ggc tgg ttg aag aag aac gag gag gct<br>Thr Ala Met Pro Leu Pro Gly Trp Leu Lys Lys Asn Glu Glu Ala<br>        1205                  1210              1215 | 3654 |
| gct gaa gaa ggc ttc aaa gac aca gaa tcc agc cct ggc tcc agc<br>Ala Glu Glu Gly Phe Lys Asp Thr Glu Ser Ser Pro Gly Ser Ser<br>        1220                  1225              1230 | 3699 |
| cct ccc agc ttg act ccc aaa ctc ctc cgc agg cag gtc act gcc<br>Pro Pro Ser Leu Thr Pro Lys Leu Leu Arg Arg Gln Val Thr Ala | 3744 |

```
                    1235                1240                1245
     tct cct tcc tct ggc ctc tct cac aag aaa gag gcc acc aag ggc         3789
     Ser Pro Ser Ser Gly Leu Ser His Lys Lys Glu Ala Thr Lys Gly
         1250                1255                1260 agt gcc tca ggc atg ggg act ccg gcc act gca gag cca gca ccc         3834
     Ser Ala Ser Gly Met Gly Thr Pro Ala Thr Ala Glu Pro Ala Pro
         1265                1270                1275 ccc agc aac aaa gtg ggc ctc agc aag gcc tcc tct gag gag atg         3879
     Pro Ser Asn Lys Val Gly Leu Ser Lys Ala Ser Ser Glu Glu Met
         1280                1285                1290 cgc gta agg agg cac aag cac agc tcg gag tcc cca ggg aga gac         3924
     Arg Val Arg Arg His Lys His Ser Ser Glu Ser Pro Gly Arg Asp
         1295                1300                1305 aag ggg cga ctg gct aag ctc aag cct gcc ccg ccg cct cct cct         3969
     Lys Gly Arg Leu Ala Lys Leu Lys Pro Ala Pro Pro Pro Pro Pro
         1310                1315                1320 gcc tgc aca gga aaa gca ggc aag ccc gca cag agc ccc agc caa         4014
     Ala Cys Thr Gly Lys Ala Gly Lys Pro Ala Gln Ser Pro Ser Gln
         1325                1330                1335 gag gcc ggg gag gca ggg ggg ccc aca aag aca aaa tgc acg agt         4059
     Glu Ala Gly Glu Ala Gly Gly Pro Thr Lys Thr Lys Cys Thr Ser
         1340                1345                1350 ctg gct atg gat gct gtg aac act gac ccc acc aag gcc ggc cca         4104
     Leu Ala Met Asp Ala Val Asn Thr Asp Pro Thr Lys Ala Gly Pro
         1355                1360                1365 cct gga gaa gga ctg aga aag cct gtg ccc cca tct gtg cca aag         4149
     Pro Gly Glu Gly Leu Arg Lys Pro Val Pro Pro Ser Val Pro Lys
         1370                1375                1380 ccc cag tcg acg gga gga gga gga gac tac aag gac gac gat gac         4194
     Pro Gln Ser Thr Gly Gly Gly Gly Asp Tyr Lys Asp Asp Asp Asp
         1385                1390                1395 aag gga gga gga gga tcg acg gct aag cct cca ggg act ccc acc         4239
     Lys Gly Gly Gly Gly Ser Thr Ala Lys Pro Pro Gly Thr Pro Thr
         1400                1405                1410 agc ccg gtc tcc acc ccc tcc aca gca cca gct cct tca ccc ctg         4284
     Ser Pro Val Ser Thr Pro Ser Thr Ala Pro Ala Pro Ser Pro Leu
         1415                1420                1425 gct ggg gac cag cag cca tct tct gcc gcc ttc atc ccc ctc ata         4329
     Ala Gly Asp Gln Gln Pro Ser Ser Ala Ala Phe Ile Pro Leu Ile
         1430                1435                1440 tca acc cgt gtg tct ctt agg aag acc cgc cag ccg cca gag cgc         4374
     Ser Thr Arg Val Ser Leu Arg Lys Thr Arg Gln Pro Pro Glu Arg
         1445                1450                1455 att gcc agt ggc acc atc acc aag ggt gtg gtt ctg gac agt act         4419
     Ile Ala Ser Gly Thr Ile Thr Lys Gly Val Val Leu Asp Ser Thr
         1460                1465                1470 gag gcc ctg tgc ctt gcc atc tcc cgg aac tca gag cag atg gcc         4464
     Glu Ala Leu Cys Leu Ala Ile Ser Arg Asn Ser Glu Gln Met Ala
         1475                1480                1485 agc cac agt gct gta ctg gag gct ggc aag aac ctg tac act ttc         4509
     Ser His Ser Ala Val Leu Glu Ala Gly Lys Asn Leu Tyr Thr Phe
         1490                1495                1500 tgt gtg agc tat gtg gac tct atc cag cag atg agg aac aag ttt         4554
     Cys Val Ser Tyr Val Asp Ser Ile Gln Gln Met Arg Asn Lys Phe
         1505                1510                1515 gcc ttc cgt gag gct atc aac aag ctg gag agc aac ctc cga gag         4599
     Ala Phe Arg Glu Ala Ile Asn Lys Leu Glu Ser Asn Leu Arg Glu
         1520                1525                1530 gct cag atc tgc cct gcc aca gcc tcc agt ggg cca gct gcc acc         4644
```

```
Ala Gln  Ile Cys Pro Ala Thr  Ala Ser Ser Gly Pro  Ala Ala Thr
    1535             1540                 1545 caa gac ttc agc aag ctg ctc  agc tct gtg aag gag  atc agc gac      4689
Gln Asp Phe Ser Lys Leu Leu  Ser Ser Val Lys Glu  Ile Ser Asp
    1550             1555                 1560 att gtc cgg agg tag c                                              4705
Ile Val Arg Arg
    1565
```

<210> SEQ ID NO 2
<211> LENGTH: 1567
<212> TYPE: PRT
<213> ORGANISM: Homo sapien/ Mus musculus

<400> SEQUENCE: 2

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320
```

-continued

```
Phe Glu Asp Cys Gly Gly Gly Tyr Thr Pro Asp Cys Ser Ser Asn Glu
            325                 330                 335

Asn Leu Thr Ser Ser Glu Asp Phe Ser Ser Gly Gln Ser Ser Arg
        340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
        435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Gly Thr Glu
            500                 505                 510

Lys Leu Arg Val Leu Gly Tyr Asn His Asn Gly Glu Trp Cys Glu Ala
        515                 520                 525

Gln Thr Lys Asn Gly Gln Gly Trp Val Pro Ser Asn Tyr Ile Thr Pro
    530                 535                 540

Val Asn Ser Leu Glu Lys His Ser Trp Tyr His Gly Pro Val Ser Arg
545                 550                 555                 560

Asn Ala Ala Glu Tyr Leu Leu Ser Ser Gly Ile Asn Gly Ser Phe Leu
                565                 570                 575

Val Arg Glu Ser Glu Ser Ser Pro Gly Gln Arg Ser Ile Ser Leu Arg
            580                 585                 590

Tyr Glu Gly Arg Val Tyr His Tyr Arg Ile Asn Thr Ala Ser Asp Gly
        595                 600                 605

Lys Leu Tyr Val Ser Ser Glu Ser Arg Phe Asn Thr Leu Ala Glu Leu
    610                 615                 620

Val His His Ser Thr Val Ala Asp Gly Leu Ile Thr Thr Leu His
625                 630                 635                 640

Tyr Pro Ala Pro Lys Arg Asn Lys Pro Thr Ile Tyr Gly Val Ser Pro
                645                 650                 655

Asn Tyr Asp Lys Trp Glu Met Glu Arg Thr Asp Ile Thr Met Lys His
            660                 665                 670

Lys Leu Gly Gly Gly Gln Tyr Gly Glu Val Tyr Glu Gly Val Trp Lys
        675                 680                 685

Lys Tyr Ser Leu Thr Val Ala Val Lys Thr Leu Lys Glu Asp Thr Met
    690                 695                 700

Glu Val Glu Glu Phe Leu Lys Glu Ala Ala Val Met Lys Glu Ile Lys
705                 710                 715                 720

His Pro Asn Leu Val Gln Leu Leu Gly Val Cys Thr Arg Glu Pro Pro
                725                 730                 735

Phe Tyr Ile Ile Thr Glu Phe Met Thr Tyr Gly Asn Leu Leu Asp Tyr
```

-continued

```
                740                 745                 750
Leu Arg Glu Cys Asn Arg Gln Glu Val Ser Ala Val Val Leu Leu Tyr
            755                 760                 765
Met Ala Thr Gln Ile Ser Ser Ala Met Glu Tyr Leu Glu Lys Lys Asn
        770                 775                 780
Phe Ile His Arg Asp Leu Ala Ala Arg Asn Cys Leu Val Gly Glu Asn
785                 790                 795                 800
His Leu Val Lys Val Ala Asp Phe Gly Leu Ser Arg Leu Met Thr Gly
                805                 810                 815
Asp Thr Tyr Thr Ala His Ala Gly Ala Lys Phe Pro Ile Lys Trp Thr
            820                 825                 830
Ala Pro Glu Ser Leu Ala Tyr Asn Lys Phe Ser Ile Lys Ser Asp Val
        835                 840                 845
Trp Ala Phe Gly Val Leu Leu Trp Glu Ile Ala Thr Tyr Gly Met Ser
850                 855                 860
Pro Tyr Pro Gly Ile Asp Leu Ser Gln Val Tyr Glu Leu Leu Glu Lys
865                 870                 875                 880
Asp Tyr Arg Met Glu Arg Pro Glu Gly Cys Pro Glu Lys Val Tyr Glu
                885                 890                 895
Leu Met Arg Ala Cys Trp Gln Trp Asn Pro Ser Asp Arg Pro Ser Phe
            900                 905                 910
Ala Glu Ile His Gln Ala Phe Glu Thr Met Phe Gln Glu Ser Ser Ile
        915                 920                 925
Ser Asp Glu Val Glu Lys Glu Leu Gly Lys Arg Gly Thr Arg Gly Gly
    930                 935                 940
Ala Gly Ser Met Leu Gln Ala Pro Glu Leu Pro Thr Lys Thr Arg Thr
945                 950                 955                 960
Cys Arg Arg Ala Ala Glu Gln Lys Asp Ala Pro Asp Thr Pro Glu Leu
                965                 970                 975
Leu His Thr Lys Gly Leu Gly Glu Ser Asp Ala Leu Asp Ser Glu Pro
            980                 985                 990
Ala Val Ser Pro Leu Leu Pro Arg Lys Glu Arg Gly Pro Pro Asp Gly
        995                 1000                1005
Ser Leu Asn Glu Asp Glu Arg Leu Leu Pro Arg Asp Arg Lys Thr
    1010                1015                1020
Asn Leu Phe Ser Ala Leu Ile Lys Lys Lys Lys Met Ala Pro
    1025                1030                1035
Thr Pro Pro Lys Arg Ser Ser Phe Arg Glu Met Asp Gly Gln
    1040                1045                1050
Pro Asp Arg Arg Gly Ala Ser Glu Asp Asp Ser Arg Glu Leu Cys
    1055                1060                1065
Asn Gly Pro Pro Ala Leu Thr Ser Asp Ala Ala Glu Pro Thr Lys
    1070                1075                1080
Ser Pro Lys Ala Ser Asn Gly Ala Gly Val Pro Asn Gly Ala Phe
    1085                1090                1095
Arg Glu Pro Gly Asn Ser Gly Phe Arg Ser Pro His Met Trp Lys
    1100                1105                1110
Lys Ser Ser Thr Leu Thr Gly Ser Arg Leu Ala Ala Ala Glu Glu
    1115                1120                1125
Glu Ser Gly Met Ser Ser Ser Lys Arg Phe Leu Arg Ser Cys Ser
    1130                1135                1140
Ala Ser Cys Met Pro His Gly Ala Arg Asp Thr Glu Trp Arg Ser
    1145                1150                1155
```

-continued

```
Val Thr Leu Pro Arg Asp Leu Pro Ser Ala Gly Lys Gln Phe Asp
    1160                1165                1170

Ser Ser Thr Phe Gly Gly His Lys Ser Glu Lys Pro Ala Leu Pro
    1175                1180                1185

Arg Lys Arg Thr Ser Glu Ser Arg Ser Glu Gln Val Ala Lys Ser
    1190                1195                1200

Thr Ala Met Pro Leu Pro Gly Trp Leu Lys Lys Asn Glu Glu Ala
    1205                1210                1215

Ala Glu Glu Gly Phe Lys Asp Thr Glu Ser Ser Pro Gly Ser Ser
    1220                1225                1230

Pro Pro Ser Leu Thr Pro Lys Leu Leu Arg Arg Gln Val Thr Ala
    1235                1240                1245

Ser Pro Ser Ser Gly Leu Ser His Lys Lys Glu Ala Thr Lys Gly
    1250                1255                1260

Ser Ala Ser Gly Met Gly Thr Pro Ala Thr Ala Glu Pro Ala Pro
    1265                1270                1275

Pro Ser Asn Lys Val Gly Leu Ser Lys Ala Ser Ser Glu Glu Met
    1280                1285                1290

Arg Val Arg Arg His Lys His Ser Ser Glu Ser Pro Gly Arg Asp
    1295                1300                1305

Lys Gly Arg Leu Ala Lys Leu Lys Pro Ala Pro Pro Pro Pro Pro
    1310                1315                1320

Ala Cys Thr Gly Lys Ala Gly Lys Pro Ala Gln Ser Pro Ser Gln
    1325                1330                1335

Glu Ala Gly Glu Ala Gly Gly Pro Thr Lys Thr Lys Cys Thr Ser
    1340                1345                1350

Leu Ala Met Asp Ala Val Asn Thr Asp Pro Thr Lys Ala Gly Pro
    1355                1360                1365

Pro Gly Glu Gly Leu Arg Lys Pro Val Pro Pro Ser Val Pro Lys
    1370                1375                1380

Pro Gln Ser Thr Gly Gly Gly Gly Asp Tyr Lys Asp Asp Asp Asp
    1385                1390                1395

Lys Gly Gly Gly Gly Ser Thr Ala Lys Pro Pro Gly Thr Pro Thr
    1400                1405                1410

Ser Pro Val Ser Thr Pro Ser Thr Ala Pro Ala Pro Ser Pro Leu
    1415                1420                1425

Ala Gly Asp Gln Gln Pro Ser Ser Ala Ala Phe Ile Pro Leu Ile
    1430                1435                1440

Ser Thr Arg Val Ser Leu Arg Lys Thr Arg Gln Pro Pro Glu Arg
    1445                1450                1455

Ile Ala Ser Gly Thr Ile Thr Lys Gly Val Val Leu Asp Ser Thr
    1460                1465                1470

Glu Ala Leu Cys Leu Ala Ile Ser Arg Asn Ser Glu Gln Met Ala
    1475                1480                1485

Ser His Ser Ala Val Leu Glu Ala Gly Lys Asn Leu Tyr Thr Phe
    1490                1495                1500

Cys Val Ser Tyr Val Asp Ser Ile Gln Gln Met Arg Asn Lys Phe
    1505                1510                1515

Ala Phe Arg Glu Ala Ile Asn Lys Leu Glu Ser Asn Leu Arg Glu
    1520                1525                1530

Ala Gln Ile Cys Pro Ala Thr Ala Ser Ser Gly Pro Ala Ala Thr
    1535                1540                1545
```

```
Gln Asp Phe Ser Lys Leu Leu Ser Ser Val Lys Glu Ile Ser Asp
    1550                1555                1560

Ile Val Arg Arg
    1565

<210> SEQ ID NO 3
<211> LENGTH: 4786
<212> TYPE: DNA
<213> ORGANISM: Homo sapien/ Mus musculus
<220> FEATURE:
<221> NAME/KEY: CDS
<222> LOCATION: (1)..(4785)
<223> OTHER INFORMATION:

<400> SEQUENCE: 3 atg gtg gac ccg gtg ggc ttc gcg gag gcg tgg aag gcg cag ttc ccg       48
Met Val Asp Pro Val Gly Phe Ala Glu Ala Trp Lys Ala Gln Phe Pro
1               5                   10                  15 gac tca gag ccc ccg cgc atg gag ctg cgc tca gtg ggc gac atc gag       96
Asp Ser Glu Pro Pro Arg Met Glu Leu Arg Ser Val Gly Asp Ile Glu
            20                  25                  30 cag gag ctg gag cgc tgc aag gcc tcc att cgg cgc ctg gag cag gag      144
Gln Glu Leu Glu Arg Cys Lys Ala Ser Ile Arg Arg Leu Glu Gln Glu
        35                  40                  45 gtg aac cag gag cgc ttc cgc atg atc tac ctg cag acg ttg ctg gcc      192
Val Asn Gln Glu Arg Phe Arg Met Ile Tyr Leu Gln Thr Leu Leu Ala
    50                  55                  60 aag gaa aag aag agc tat gac cgg cag cga tgg ggc ttc cgg cgc gcg      240
Lys Glu Lys Lys Ser Tyr Asp Arg Gln Arg Trp Gly Phe Arg Arg Ala
65                  70                  75                  80 gcg cag gcc ccc gac ggc gcc tcc gag ccc cga gcg tcc gcg tcg cgc      288
Ala Gln Ala Pro Asp Gly Ala Ser Glu Pro Arg Ala Ser Ala Ser Arg
                85                  90                  95 ccg cag cca gcg ccc gcc gac gga gcc gac ccg ccg ccc gcc gag gag      336
Pro Gln Pro Ala Pro Ala Asp Gly Ala Asp Pro Pro Pro Ala Glu Glu
            100                 105                 110 ccc gag gcc cgg ccc gac ggc gag ggt tct ccg ggt aag gcc agg ccc      384
Pro Glu Ala Arg Pro Asp Gly Glu Gly Ser Pro Gly Lys Ala Arg Pro
        115                 120                 125 ggg acc gcc cgc agg ccc ggg gca gcc gcg tcg ggg gaa cgg gac gac      432
Gly Thr Ala Arg Arg Pro Gly Ala Ala Ala Ser Gly Glu Arg Asp Asp
    130                 135                 140 cgg gga ccc ccc gcc agc gtg gcg gcg ctc agg tcc aac ttc gag cgg      480
Arg Gly Pro Pro Ala Ser Val Ala Ala Leu Arg Ser Asn Phe Glu Arg
145                 150                 155                 160 atc cgg aag ggc cat ggc cag ccc ggg gcg gac gcc gag aag ccc ttc      528
Ile Arg Lys Gly His Gly Gln Pro Gly Ala Asp Ala Glu Lys Pro Phe
                165                 170                 175 tac gtg aac gtc gag ttt cac cac gag cgc ggc ctg gtg aag gtc aac      576
Tyr Val Asn Val Glu Phe His His Glu Arg Gly Leu Val Lys Val Asn
            180                 185                 190 gac aaa gag gtg tcg gac cgc atc agc tcc ctt ggc agc cag gcc atg      624
Asp Lys Glu Val Ser Asp Arg Ile Ser Ser Leu Gly Ser Gln Ala Met
        195                 200                 205 cag atg gag cgc aaa aag tcc cag cac ggc gcg ggc tcg agc gtg ggg      672
Gln Met Glu Arg Lys Lys Ser Gln His Gly Ala Gly Ser Ser Val Gly
    210                 215                 220 gat gca tcc agg ccc cct tac cgg gga cgc tcc tcg gag agc agc tgc      720
Asp Ala Ser Arg Pro Pro Tyr Arg Gly Arg Ser Ser Glu Ser Ser Cys
225                 230                 235                 240 ggc gtc gac ggc gac tac gag gac gcc gag ttg aac ccc cgc ttc ctg      768
```

```
                                                            -continued

Gly Val Asp Gly Asp Tyr Glu Asp Ala Glu Leu Asn Pro Arg Phe Leu
                    245                 250                 255 aag gac aac ctg atc gac gcc aat ggc ggt agc agg ccc cct tgg ccg         816
Lys Asp Asn Leu Ile Asp Ala Asn Gly Gly Ser Arg Pro Pro Trp Pro
                260                 265                 270 ccc ctg gag tac cag ccc tac cag agc atc tac gtc ggg ggc atc atg         864
Pro Leu Glu Tyr Gln Pro Tyr Gln Ser Ile Tyr Val Gly Gly Ile Met
                275                 280                 285 gaa ggg gag ggc aag ggc ccg ctc ctg cgc agc cag agc acc tct gag         912
Glu Gly Glu Gly Lys Gly Pro Leu Leu Arg Ser Gln Ser Thr Ser Glu
            290                 295                 300 cag gag aag cgc ctt acc tgg ccc cgc agg tcc tac tcc ccc cgg agt         960
Gln Glu Lys Arg Leu Thr Trp Pro Arg Arg Ser Tyr Ser Pro Arg Ser
305                 310                 315                 320 ttt gag gat tgc gga ggc ggc tat acc ccg gac tgc agc tcc aat gag        1008
Phe Glu Asp Cys Gly Gly Gly Tyr Thr Pro Asp Cys Ser Ser Asn Glu
                325                 330                 335 aac ctc acc tcc agc gag gag gac ttc tcc tct ggc cag tcc agc cgc        1056
Asn Leu Thr Ser Ser Glu Glu Asp Phe Ser Ser Gly Gln Ser Ser Arg
                340                 345                 350 gtg tcc cca agc ccc acc acc tac cgc atg ttc cgg gac aaa agc cgc        1104
Val Ser Pro Ser Pro Thr Thr Tyr Arg Met Phe Arg Asp Lys Ser Arg
                355                 360                 365 tct ccc tcg cag aac tcg caa cag tcc ttc gac agc agc agt ccc ccc        1152
Ser Pro Ser Gln Asn Ser Gln Gln Ser Phe Asp Ser Ser Ser Pro Pro
            370                 375                 380 acg ccg cag tgc cat aag cgg cac cgg cac tgc ccg gtt gtc gtg tcc        1200
Thr Pro Gln Cys His Lys Arg His Arg His Cys Pro Val Val Val Ser
385                 390                 395                 400 gag gcc acc atc gtg ggc gtc cgc aag acc ggg cag atc tgg ccc aac        1248
Glu Ala Thr Ile Val Gly Val Arg Lys Thr Gly Gln Ile Trp Pro Asn
                405                 410                 415 gat gac gag ggc gcc ttc cat gga gac gca gat ggc tcg ttc gga aca        1296
Asp Asp Glu Gly Ala Phe His Gly Asp Ala Asp Gly Ser Phe Gly Thr
                420                 425                 430 cca cct gga tac ggc tgc gct gca gac cgg gca gag gag cag cgc cgg        1344
Pro Pro Gly Tyr Gly Cys Ala Ala Asp Arg Ala Glu Glu Gln Arg Arg
            435                 440                 445 cac caa gat ggg ctg ccc tac att gat gac tcg ccc tcc tca tcg ccc        1392
His Gln Asp Gly Leu Pro Tyr Ile Asp Asp Ser Pro Ser Ser Ser Pro
        450                 455                 460 cac ctc agc agc aag ggc agg ggc agc cgg gat gcg ctg gtc tcg gga        1440
His Leu Ser Ser Lys Gly Arg Gly Ser Arg Asp Ala Leu Val Ser Gly
465                 470                 475                 480 gcc ctg aag tcc act aaa gcg agt gag ctg gac ttg gaa aag ggc ttg        1488
Ala Leu Lys Ser Thr Lys Ala Ser Glu Leu Asp Leu Glu Lys Gly Leu
                485                 490                 495 gag atg aga aaa tgg gtc ctg tcg gga atc ctg gct agc ggt acc gaa        1536
Glu Met Arg Lys Trp Val Leu Ser Gly Ile Leu Ala Ser Gly Thr Glu
                500                 505                 510 aag ctc cgg gtc ttg ggt tat aat cac aat ggg gaa tgg tgt gaa gcc        1584
Lys Leu Arg Val Leu Gly Tyr Asn His Asn Gly Glu Trp Cys Glu Ala
                515                 520                 525 caa acg aaa aat ggc caa gga tgg gtc cca agc aac tac atc acc ccc        1632
Gln Thr Lys Asn Gly Gln Gly Trp Val Pro Ser Asn Tyr Ile Thr Pro
            530                 535                 540 gtc aac agc ctg gag aaa cat tcc tgg tat cat ggc cct gta tct cgg        1680
Val Asn Ser Leu Glu Lys His Ser Trp Tyr His Gly Pro Val Ser Arg
545                 550                 555                 560
```

-continued

```
aat gct gct gag tat ctg ctg agc agc gga atc aac ggc agc ttc tta    1728
Asn Ala Ala Glu Tyr Leu Leu Ser Ser Gly Ile Asn Gly Ser Phe Leu
            565                 570                 575 gtg cgg gag agt gag agt agc cct ggc cag aga tcc atc tcg ctg cgg    1776
Val Arg Glu Ser Glu Ser Ser Pro Gly Gln Arg Ser Ile Ser Leu Arg
580                 585                 590 tat gaa ggg agg gtg tac cac tac agg atc aac act gcc tct gat ggc    1824
Tyr Glu Gly Arg Val Tyr His Tyr Arg Ile Asn Thr Ala Ser Asp Gly
    595                 600                 605 aag ctg tac gtg tcc tcc gag agc cgc ttc aac act ctg gct gag tta    1872
Lys Leu Tyr Val Ser Ser Glu Ser Arg Phe Asn Thr Leu Ala Glu Leu
610                 615                 620 gtt cac cat cac tcc acg gtg gct gat ggc ctc atc acc aca ctc cac    1920
Val His His His Ser Thr Val Ala Asp Gly Leu Ile Thr Thr Leu His
625                 630                 635                 640 tac cca gct ccc aag cgc aac aag ccc act atc tac ggt gtg tcc ccc    1968
Tyr Pro Ala Pro Lys Arg Asn Lys Pro Thr Ile Tyr Gly Val Ser Pro
                645                 650                 655 aac tac gac aag tgg gaa atg gag cgc acc gac atc acc atg aag cac    2016
Asn Tyr Asp Lys Trp Glu Met Glu Arg Thr Asp Ile Thr Met Lys His
            660                 665                 670 aag ttg ggt gga ggc cag tac ggg gag gtg tac gag ggc gtt tgg aag    2064
Lys Leu Gly Gly Gly Gln Tyr Gly Glu Val Tyr Glu Gly Val Trp Lys
        675                 680                 685 aag tac agc ctc act gtg gcc gtg aag acc ttg aag gag gac acc atg    2112
Lys Tyr Ser Leu Thr Val Ala Val Lys Thr Leu Lys Glu Asp Thr Met
    690                 695                 700 gag gtg gag gag ttc ctg aag gaa gcg gcg gtg atg aag gag atc aaa    2160
Glu Val Glu Glu Phe Leu Lys Glu Ala Ala Val Met Lys Glu Ile Lys
705                 710                 715                 720 cac cct aac ctg gtg cag ctg cta ggg gtg tgt acc cgg gaa cca cca    2208
His Pro Asn Leu Val Gln Leu Leu Gly Val Cys Thr Arg Glu Pro Pro
                725                 730                 735 ttc tac ata atc act gag ttc atg acc tat ggg aac ctg ctg gac tac    2256
Phe Tyr Ile Ile Thr Glu Phe Met Thr Tyr Gly Asn Leu Leu Asp Tyr
            740                 745                 750 ctg agg gag tgt aac cgg cag gag gtg agc gcc gtg gta ctg ctc tac    2304
Leu Arg Glu Cys Asn Arg Gln Glu Val Ser Ala Val Val Leu Leu Tyr
        755                 760                 765 atg gcc aca cag atc tca tca gcc atg gag tac ttg gag aag aag aac    2352
Met Ala Thr Gln Ile Ser Ser Ala Met Glu Tyr Leu Glu Lys Lys Asn
    770                 775                 780 ttc atc cac aga gac ctt gct gcc cgg aac tgc ctg gta ggg gaa aac    2400
Phe Ile His Arg Asp Leu Ala Ala Arg Asn Cys Leu Val Gly Glu Asn
785                 790                 795                 800 cac ttg gtg aag gtg gct gat ttt ggc ctg agc agg ttg atg aca ggg    2448
His Leu Val Lys Val Ala Asp Phe Gly Leu Ser Arg Leu Met Thr Gly
                805                 810                 815 gac acc tac acg gcc cat gct gga gcc aaa ttc ccc atc aaa tgg acc    2496
Asp Thr Tyr Thr Ala His Ala Gly Ala Lys Phe Pro Ile Lys Trp Thr
            820                 825                 830 gca cct gag agc ctg gcc tac aac aag ttc tcc atc aag tcg gac gtg    2544
Ala Pro Glu Ser Leu Ala Tyr Asn Lys Phe Ser Ile Lys Ser Asp Val
        835                 840                 845 tgg gca ttt gga gta ttg ctc tgg gag att gct acc tat ggc atg tca    2592
Trp Ala Phe Gly Val Leu Leu Trp Glu Ile Ala Thr Tyr Gly Met Ser
    850                 855                 860 cct tac ccg gga att gac ctg tct cag gtt tat gag ctg ctg gaa aaa    2640
Pro Tyr Pro Gly Ile Asp Leu Ser Gln Val Tyr Glu Leu Leu Glu Lys
865                 870                 875                 880
```

-continued

| | |
|---|---|
| gac tac cgc atg gag cgc cct gaa ggc tgc ccg gag aag gtc tac gag<br>Asp Tyr Arg Met Glu Arg Pro Glu Gly Cys Pro Glu Lys Val Tyr Glu<br>                    885                    890                    895 | 2688 |
| ctc atg cga gca tgt tgg cag tgg aac ccc tct gac cgg ccc tcc ttt<br>Leu Met Arg Ala Cys Trp Gln Trp Asn Pro Ser Asp Arg Pro Ser Phe<br>    900                    905                    910 | 2736 |
| gct gaa atc cac caa gcc ttt gaa acc atg ttc cag gaa tcc agt atc<br>Ala Glu Ile His Gln Ala Phe Glu Thr Met Phe Gln Glu Ser Ser Ile<br>            915                    920                    925 | 2784 |
| tca gat gag gtg gag aag gag ctg ggg aaa cga ggc acg aga gga ggt<br>Ser Asp Glu Val Glu Lys Glu Leu Gly Lys Arg Gly Thr Arg Gly Gly<br>930                    935                    940 | 2832 |
| gct ggg agt atg ctg cag gcc cca gag ctg ccc acc aag acc aga acc<br>Ala Gly Ser Met Leu Gln Ala Pro Glu Leu Pro Thr Lys Thr Arg Thr<br>945                    950                    955                    960 | 2880 |
| tgc agg aga gca gct gag cag aaa gat gcg cct gac acc cct gag ctg<br>Cys Arg Arg Ala Ala Glu Gln Lys Asp Ala Pro Asp Thr Pro Glu Leu<br>            965                    970                    975 | 2928 |
| ctc cac acg aag ggc ctg gga gaa agc gat gca ctg gac agt gag cct<br>Leu His Thr Lys Gly Leu Gly Glu Ser Asp Ala Leu Asp Ser Glu Pro<br>                980                    985                    990 | 2976 |
| gct gta tcg cca ctg ctt cct cgg aaa gag cgc ggg ccc cca gac ggc<br>Ala Val Ser Pro Leu Leu Pro Arg Lys Glu Arg Gly Pro Pro Asp Gly<br>        995                    1000                 1005 | 3024 |
| agc cta aat gaa gat gag cgc ctt ctc ccc aga gac aga aag acc<br>Ser Leu Asn Glu Asp Glu Arg Leu Leu Pro Arg Asp Arg Lys Thr<br>       1010                 1015                 1020 | 3069 |
| aac ctg ttc agc gct ttg atc aag aag aag aag aaa atg gcg ccg<br>Asn Leu Phe Ser Ala Leu Ile Lys Lys Lys Lys Lys Met Ala Pro<br>    1025                 1030                 1035 | 3114 |
| acg ccc cct aag cgc agc agt tcc ttc cga gag atg gat ggc cag<br>Thr Pro Pro Lys Arg Ser Ser Phe Arg Glu Met Asp Gly Gln<br>       1040                 1045                 1050 | 3159 |
| cca gac cgc aga ggg gct agt gag gat gac agc agg gaa ctc tgc<br>Pro Asp Arg Arg Gly Ala Ser Glu Asp Asp Ser Arg Glu Leu Cys<br>    1055                 1060                 1065 | 3204 |
| aat gga cca cca gct ctc acc tca gac gca gca gag cct acc aag<br>Asn Gly Pro Pro Ala Leu Thr Ser Asp Ala Ala Glu Pro Thr Lys<br>    1070                 1075                 1080 | 3249 |
| tcc cca aag gcc agc aat ggg gct ggc gtc cct aat gga gcc ttc<br>Ser Pro Lys Ala Ser Asn Gly Ala Gly Val Pro Asn Gly Ala Phe<br>    1085                 1090                 1095 | 3294 |
| cgg gag ccg ggc aac tca ggc ttc cgt tct ccc cac atg tgg aaa<br>Arg Glu Pro Gly Asn Ser Gly Phe Arg Ser Pro His Met Trp Lys<br>    1100                 1105                 1110 | 3339 |
| aag tcc agc aca ctg acc ggg agc cgc ctg gct gct gcc gaa gag<br>Lys Ser Ser Thr Leu Thr Gly Ser Arg Leu Ala Ala Ala Glu Glu<br>    1115                 1120                 1125 | 3384 |
| gag agc ggc atg agc tcc agt aag cgc ttc ctg cgt tct tgt tcg<br>Glu Ser Gly Met Ser Ser Ser Lys Arg Phe Leu Arg Ser Cys Ser<br>    1130                 1135                 1140 | 3429 |
| gcc tcc tgc atg ccc cat ggg gca agg gac aca gag tgg cgg tcg<br>Ala Ser Cys Met Pro His Gly Ala Arg Asp Thr Glu Trp Arg Ser<br>    1145                 1150                 1155 | 3474 |
| gtc acg ctg cct cga gac ctg ccg tct gct ggc aag cag ttt gac<br>Val Thr Leu Pro Arg Asp Leu Pro Ser Ala Gly Lys Gln Phe Asp<br>    1160                 1165                 1170 | 3519 |
| tca tcc acc ttt gga ggg cac aaa agc gaa aag cca gct ctg cct<br>Ser Ser Thr Phe Gly Gly His Lys Ser Glu Lys Pro Ala Leu Pro | 3564 |

-continued

|  |  |  |  |
|---|---|---|---|
| 1175 | 1180 | 1185 | |
| cgg aaa cgc acc agt gag agc agg tct gag cag gtg gcc aaa agc<br>Arg Lys Arg Thr Ser Glu Ser Arg Ser Glu Gln Val Ala Lys Ser<br>1190                        1195                        1200 | | | 3609 |
| acg gcg atg ccc ctc ccc ggc tgg ttg aag aag aac gag gag gct<br>Thr Ala Met Pro Leu Pro Gly Trp Leu Lys Lys Asn Glu Glu Ala<br>1205                        1210                        1215 | | | 3654 |
| gct gaa gaa ggc ttc aaa gac aca gaa tcc agc cct ggc tcc agc<br>Ala Glu Glu Gly Phe Lys Asp Thr Glu Ser Ser Pro Gly Ser Ser<br>1220                        1225                        1230 | | | 3699 |
| cct ccc agc ttg act ccc aaa ctc ctc cgc agg cag gtc act gcc<br>Pro Pro Ser Leu Thr Pro Lys Leu Leu Arg Arg Gln Val Thr Ala<br>1235                        1240                        1245 | | | 3744 |
| tct cct tcc tct ggc ctc tct cac aag aaa gag gcc acc aag ggc<br>Ser Pro Ser Ser Gly Leu Ser His Lys Lys Glu Ala Thr Lys Gly<br>1250                        1255                        1260 | | | 3789 |
| agt gcc tca ggc atg ggg act ccg gcc act gca gag cca gca ccc<br>Ser Ala Ser Gly Met Gly Thr Pro Ala Thr Ala Glu Pro Ala Pro<br>1265                        1270                        1275 | | | 3834 |
| ccc agc aac aaa gtg ggc ctc agc aag gcc tcc tct gag gag atg<br>Pro Ser Asn Lys Val Gly Leu Ser Lys Ala Ser Ser Glu Glu Met<br>1280                        1285                        1290 | | | 3879 |
| cgc gta agg agg cac aag cac agc tcg gag tcc cca ggg aga gac<br>Arg Val Arg Arg His Lys His Ser Ser Glu Ser Pro Gly Arg Asp<br>1295                        1300                        1305 | | | 3924 |
| aag ggg cga ctg gct aag ctc aag cct gcc ccg ccg cct cct cct<br>Lys Gly Arg Leu Ala Lys Leu Lys Pro Ala Pro Pro Pro Pro Pro<br>1310                        1315                        1320 | | | 3969 |
| gcc tgc aca gga aaa gca ggc aag ccc gca cag agc ccc agc caa<br>Ala Cys Thr Gly Lys Ala Gly Lys Pro Ala Gln Ser Pro Ser Gln<br>1325                        1330                        1335 | | | 4014 |
| gag gcc ggg gag gca ggg ggg ccc aca aag aca aaa tgc acg agt<br>Glu Ala Gly Glu Ala Gly Gly Pro Thr Lys Thr Lys Cys Thr Ser<br>1340                        1345                        1350 | | | 4059 |
| ctg gct atg gat gct gtg aac act gac ccc acc aag gcc ggc cca<br>Leu Ala Met Asp Ala Val Asn Thr Asp Pro Thr Lys Ala Gly Pro<br>1355                        1360                        1365 | | | 4104 |
| cct gga gaa gga ctg aga aag cct gtg ccc cca tct gtg cca aag<br>Pro Gly Glu Gly Leu Arg Lys Pro Val Pro Pro Ser Val Pro Lys<br>1370                        1375                        1380 | | | 4149 |
| ccc cag tcg acg ggc gga ccc aag aaa aag agg aag gtg cct aaa<br>Pro Gln Ser Thr Gly Gly Pro Lys Lys Lys Arg Lys Val Pro Lys<br>1385                        1390                        1395 | | | 4194 |
| aag aaa cgc aaa gtg cca aag aag aag cgg aag gtg ggt ggg tcg<br>Lys Lys Arg Lys Val Pro Lys Lys Lys Arg Lys Val Gly Gly Ser<br>1400                        1405                        1410 | | | 4239 |
| acg gga gga gga gga gac tac aag gac gac gat gac aag gga gga<br>Thr Gly Gly Gly Gly Asp Tyr Lys Asp Asp Asp Asp Lys Gly Gly<br>1415                        1420                        1425 | | | 4284 |
| gga gga tcg acg gct aag cct cca ggg act ccc acc agc ccg gtc<br>Gly Gly Ser Thr Ala Lys Pro Pro Gly Thr Pro Thr Ser Pro Val<br>1430                        1435                        1440 | | | 4329 |
| tcc acc ccc tcc aca gca cca gct cct tca ccc ctg gct ggg gac<br>Ser Thr Pro Ser Thr Ala Pro Ala Pro Ser Pro Leu Ala Gly Asp<br>1445                        1450                        1455 | | | 4374 |
| cag cag cca tct tct gcc gcc ttc atc ccc ctc ata tca acc cgt<br>Gln Gln Pro Ser Ser Ala Ala Phe Ile Pro Leu Ile Ser Thr Arg<br>1460                        1465                        1470 | | | 4419 |
| gtg tct ctt agg aag acc cgc cag ccg cca gag cgc att gcc agt | | | 4464 |

```
                        Val Ser Leu Arg Lys Thr Arg Gln Pro Pro Glu Arg Ile Ala Ser
                            1475                1480                1485 ggc acc atc acc aag ggt gtg gtt ctg gac agt act gag gcc ctg         4509
Gly Thr Ile Thr Lys Gly Val Val Leu Asp Ser Thr Glu Ala Leu
    1490                1495                1500 tgc ctt gcc atc tcc cgg aac tca gag cag atg gcc agc cac agt         4554
Cys Leu Ala Ile Ser Arg Asn Ser Glu Gln Met Ala Ser His Ser
    1505                1510                1515 gct gta ctg gag gct ggc aag aac ctg tac act ttc tgt gtg agc         4599
Ala Val Leu Glu Ala Gly Lys Asn Leu Tyr Thr Phe Cys Val Ser
    1520                1525                1530 tat gtg gac tct atc cag cag atg agg aac aag ttt gcc ttc cgt         4644
Tyr Val Asp Ser Ile Gln Gln Met Arg Asn Lys Phe Ala Phe Arg
    1535                1540                1545 gag gct atc aac aag ctg gag agc aac ctc cga gag gct cag atc         4689
Glu Ala Ile Asn Lys Leu Glu Ser Asn Leu Arg Glu Ala Gln Ile
    1550                1555                1560 tgc cct gcc aca gcc tcc agt ggg cca gct gcc acc caa gac ttc         4734
Cys Pro Ala Thr Ala Ser Ser Gly Pro Ala Ala Thr Gln Asp Phe
    1565                1570                1575 agc aag ctg ctc agc tct gtg aag gag atc agc gac att gtc cgg         4779
Ser Lys Leu Leu Ser Ser Val Lys Glu Ile Ser Asp Ile Val Arg
    1580                1585                1590 agg tag c                                                            4786
Arg
```

<210> SEQ ID NO 4
<211> LENGTH: 1594
<212> TYPE: PRT
<213> ORGANISM: Homo sapien/ Mus musculus

<400> SEQUENCE: 4

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
```

-continued

```
                195                 200                 205
Gln Met Glu Arg Lys Ser Gln His Gly Ala Gly Ser Ser Val Gly
    210                 215                 220

Asp Ala Ser Arg Pro Pro Tyr Arg Gly Arg Ser Ser Glu Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
        435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Gly Thr Glu
            500                 505                 510

Lys Leu Arg Val Leu Gly Tyr Asn His Asn Gly Glu Trp Cys Glu Ala
        515                 520                 525

Gln Thr Lys Asn Gly Gln Gly Trp Val Pro Ser Asn Tyr Ile Thr Pro
    530                 535                 540

Val Asn Ser Leu Glu Lys His Ser Trp Tyr His Gly Pro Val Ser Arg
545                 550                 555                 560

Asn Ala Ala Glu Tyr Leu Leu Ser Ser Gly Ile Asn Gly Ser Phe Leu
                565                 570                 575

Val Arg Glu Ser Glu Ser Ser Pro Gly Gln Arg Ser Ile Ser Leu Arg
            580                 585                 590

Tyr Glu Gly Arg Val Tyr His Tyr Arg Ile Asn Thr Ala Ser Asp Gly
        595                 600                 605

Lys Leu Tyr Val Ser Ser Glu Ser Arg Phe Asn Thr Leu Ala Glu Leu
    610                 615                 620
```

```
Val His His His Ser Thr Val Ala Asp Gly Leu Ile Thr Thr Leu His
625                 630                 635                 640

Tyr Pro Ala Pro Lys Arg Asn Lys Pro Thr Ile Tyr Gly Val Ser Pro
            645                 650                 655

Asn Tyr Asp Lys Trp Glu Met Glu Arg Thr Asp Ile Thr Met Lys His
            660                 665                 670

Lys Leu Gly Gly Gly Gln Tyr Gly Val Tyr Glu Gly Val Trp Lys
        675                 680                 685

Lys Tyr Ser Leu Thr Val Ala Val Lys Thr Leu Lys Glu Asp Thr Met
        690                 695                 700

Glu Val Glu Glu Phe Leu Lys Glu Ala Ala Val Met Lys Glu Ile Lys
705                 710                 715                 720

His Pro Asn Leu Val Gln Leu Leu Gly Val Cys Thr Arg Glu Pro Pro
                725                 730                 735

Phe Tyr Ile Ile Thr Glu Phe Met Thr Tyr Gly Asn Leu Leu Asp Tyr
                740                 745                 750

Leu Arg Glu Cys Asn Arg Gln Glu Val Ser Ala Val Val Leu Leu Tyr
            755                 760                 765

Met Ala Thr Gln Ile Ser Ser Ala Met Glu Tyr Leu Glu Lys Lys Asn
    770                 775                 780

Phe Ile His Arg Asp Leu Ala Ala Arg Asn Cys Leu Val Gly Glu Asn
785                 790                 795                 800

His Leu Val Lys Val Ala Asp Phe Gly Leu Ser Arg Leu Met Thr Gly
                805                 810                 815

Asp Thr Tyr Thr Ala His Ala Gly Ala Lys Phe Pro Ile Lys Trp Thr
                820                 825                 830

Ala Pro Glu Ser Leu Ala Tyr Asn Lys Phe Ser Ile Lys Ser Asp Val
            835                 840                 845

Trp Ala Phe Gly Val Leu Leu Trp Glu Ile Ala Thr Tyr Gly Met Ser
850                 855                 860

Pro Tyr Pro Gly Ile Asp Leu Ser Gln Val Tyr Glu Leu Leu Glu Lys
865                 870                 875                 880

Asp Tyr Arg Met Glu Arg Pro Glu Gly Cys Pro Glu Lys Val Tyr Glu
                885                 890                 895

Leu Met Arg Ala Cys Trp Gln Trp Asn Pro Ser Asp Arg Pro Ser Phe
            900                 905                 910

Ala Glu Ile His Gln Ala Phe Glu Thr Met Phe Gln Glu Ser Ser Ile
            915                 920                 925

Ser Asp Glu Val Glu Lys Glu Leu Gly Lys Arg Gly Thr Arg Gly Gly
    930                 935                 940

Ala Gly Ser Met Leu Gln Ala Pro Glu Leu Pro Thr Lys Thr Arg Thr
945                 950                 955                 960

Cys Arg Arg Ala Ala Glu Gln Lys Asp Ala Pro Asp Thr Pro Glu Leu
            965                 970                 975

Leu His Thr Lys Gly Leu Gly Glu Ser Asp Ala Leu Asp Ser Glu Pro
        980                 985                 990

Ala Val Ser Pro Leu Leu Pro Arg Lys Glu Arg Gly Pro Pro Asp Gly
        995                 1000                1005

Ser Leu Asn Glu Asp Glu Arg Leu Leu Pro Arg Asp Arg Lys Thr
    1010                1015                1020

Asn Leu Phe Ser Ala Leu Ile Lys Lys Lys Lys Met Ala Pro
    1025                1030                1035
```

-continued

```
Thr Pro Pro Lys Arg Ser Ser Ser Phe Arg Glu Met Asp Gly Gln
1040                1045                1050

Pro Asp Arg Arg Gly Ala Ser Glu Asp Ser Arg Glu Leu Cys
1055                1060                1065

Asn Gly Pro Pro Ala Leu Thr Ser Asp Ala Ala Glu Pro Thr Lys
1070                1075                1080

Ser Pro Lys Ala Ser Asn Gly Ala Gly Val Pro Asn Gly Ala Phe
1085                1090                1095

Arg Glu Pro Gly Asn Ser Gly Phe Arg Ser Pro His Met Trp Lys
1100                1105                1110

Lys Ser Ser Thr Leu Thr Gly Ser Arg Leu Ala Ala Ala Glu Glu
1115                1120                1125

Glu Ser Gly Met Ser Ser Ser Lys Arg Phe Leu Arg Ser Cys Ser
1130                1135                1140

Ala Ser Cys Met Pro His Gly Ala Arg Asp Thr Glu Trp Arg Ser
1145                1150                1155

Val Thr Leu Pro Arg Asp Leu Pro Ser Ala Gly Lys Gln Phe Asp
1160                1165                1170

Ser Ser Thr Phe Gly Gly His Lys Ser Glu Lys Pro Ala Leu Pro
1175                1180                1185

Arg Lys Arg Thr Ser Glu Ser Arg Ser Glu Gln Val Ala Lys Ser
1190                1195                1200

Thr Ala Met Pro Leu Pro Gly Trp Leu Lys Lys Asn Glu Glu Ala
1205                1210                1215

Ala Glu Glu Gly Phe Lys Asp Thr Glu Ser Ser Pro Gly Ser Ser
1220                1225                1230

Pro Pro Ser Leu Thr Pro Lys Leu Leu Arg Arg Gln Val Thr Ala
1235                1240                1245

Ser Pro Ser Ser Gly Leu Ser His Lys Lys Glu Ala Thr Lys Gly
1250                1255                1260

Ser Ala Ser Gly Met Gly Thr Pro Ala Thr Ala Glu Pro Ala Pro
1265                1270                1275

Pro Ser Asn Lys Val Gly Leu Ser Lys Ala Ser Ser Glu Glu Met
1280                1285                1290

Arg Val Arg Arg His Lys His Ser Ser Glu Ser Pro Gly Arg Asp
1295                1300                1305

Lys Gly Arg Leu Ala Lys Leu Lys Pro Ala Pro Pro Pro Pro Pro
1310                1315                1320

Ala Cys Thr Gly Lys Ala Gly Lys Pro Ala Gln Ser Pro Ser Gln
1325                1330                1335

Glu Ala Gly Glu Ala Gly Gly Pro Thr Lys Thr Lys Cys Thr Ser
1340                1345                1350

Leu Ala Met Asp Ala Val Asn Thr Asp Pro Thr Lys Ala Gly Pro
1355                1360                1365

Pro Gly Glu Gly Leu Arg Lys Pro Val Pro Ser Val Pro Lys
1370                1375                1380

Pro Gln Ser Thr Gly Gly Pro Lys Lys Lys Arg Lys Val Pro Lys
1385                1390                1395

Lys Lys Arg Lys Val Pro Lys Lys Arg Lys Val Gly Gly Ser
1400                1405                1410

Thr Gly Gly Gly Gly Asp Tyr Lys Asp Asp Asp Lys Gly Gly
1415                1420                1425

Gly Gly Ser Thr Ala Lys Pro Pro Gly Thr Pro Thr Ser Pro Val
```

-continued

```
            1430                1435                1440
Ser  Thr  Pro  Ser  Thr  Ala  Pro  Ala  Pro  Ser  Pro  Leu  Ala  Gly  Asp
            1445                1450                1455

Gln  Gln  Pro  Ser  Ser  Ala  Ala  Phe  Ile  Pro  Leu  Ile  Ser  Thr  Arg
            1460                1465                1470

Val  Ser  Leu  Arg  Lys  Thr  Arg  Gln  Pro  Pro  Glu  Arg  Ile  Ala  Ser
            1475                1480                1485

Gly  Thr  Ile  Thr  Lys  Gly  Val  Val  Leu  Asp  Ser  Thr  Glu  Ala  Leu
            1490                1495                1500

Cys  Leu  Ala  Ile  Ser  Arg  Asn  Ser  Glu  Gln  Met  Ala  Ser  His  Ser
            1505                1510                1515

Ala  Val  Leu  Glu  Ala  Gly  Lys  Asn  Leu  Tyr  Thr  Phe  Cys  Val  Ser
            1520                1525                1530

Tyr  Val  Asp  Ser  Ile  Gln  Gln  Met  Arg  Asn  Lys  Phe  Ala  Phe  Arg
            1535                1540                1545

Glu  Ala  Ile  Asn  Lys  Leu  Glu  Ser  Asn  Leu  Arg  Glu  Ala  Gln  Ile
            1550                1555                1560

Cys  Pro  Ala  Thr  Ala  Ser  Ser  Gly  Pro  Ala  Ala  Thr  Gln  Asp  Phe
            1565                1570                1575

Ser  Lys  Leu  Leu  Ser  Ser  Val  Lys  Glu  Ile  Ser  Asp  Ile  Val  Arg
            1580                1585                1590

Arg
```

STRATEGY FOR LEUKEMIA THERAPY

CROSS-REFERENCES TO RELATED APPLICATIONS

This application claims the benefit of priority of U.S. provisional application Ser. No. 60/215,595 filed Jun. 30, 2000 which is incorporated herein by reference in its entirety.

GOVERNMENT INTEREST

The invention was made with government support from the National Institutes of Health under grant numbers CA 43054 and HL57900.

BACKGROUND OF THE INVENTION

Chronic myeloid leukemia (CML) is a hematological stem cell disorder characterized by excessive proliferation of cells of the myeloid lineage. The hallmark of CML is the Philadelphia chromosome, which arises from a reciprocal translocation between chromosomes 9 and 22 (Rowley, 1973). The molecular consequence of this translocation is the replacement of the first exon of c-Abl with sequences from the Bcr gene resulting in a Bcr-Abl fusion gene whose protein product shows enhanced tyrosine kinase activity (Bartram, et al., 1983; Ben-Neriah, et al., 1986; Heisterkamp et al, 1983; Konopka, et al., 1984; Shtivelman et al., 1985). The Bcr-Abl oncoprotein in CML is a 210-kD protein that contains 902 or 927 amino acids of Bcr fused to the expression product of exons 2–11 of c-Abl (Ben-Neriah, et al., 1986; Shtivelman et al., 1985). Found in 95% of patients with CML, p210 Bcr-Abl is also present in approximately 5–10% of adults with acute leukemia for whom there is no evidence of antecedent CML (Kruzrock, et al., 1988). Another Bcr-Abl fusion protein of 185 kD containing Bcr sequences from exon 1 (426 amino acids) fused to exons 2–11 of c-Abl, occurs in 10% of adult cases and 5–10% of pediatric cases of acute lymphoblastic leukemia (ALL), but not in CML (Clark, et al., 1988; Hermans et al., 1987). It is believed that this single chromosomal rearrangement is sufficient to initiate the development of these diseases and may be the only molecular abnormality in early stage disease.

Protein kinases are a large family of homologous proteins comprising 2 major subfamilies, the protein serine/threonine kinases and protein tyrosine kinases (PTKs). Protein kinases function as components of signal transduction pathways, playing a central role in diverse biological processes such as control of cell growth, metabolism, differentiation, and apoptosis. The development of selective protein kinase inhibitors that can block or modulate diseases with abnormalities in these signaling pathways is considered a promising approach for drug development. However, due to the structural and functional similarities of kinases, it is virtually impossible to make an inhibitor specific to a single kinase. Because of their deregulation in human cancers, Bcr-Abl, epidermal growth factor receptor (EGFR), HER2, and protein kinase C (PKC), were among the first protein kinases considered as targets for the development of selective inhibitors. As protein kinases have been implicated in more human cancers (Kolibaba and Drucker, 1997), drug-discovery efforts have been extended and several first-generation small-molecule inhibitors are now in various stages of development. A selection of these agents is shown in FIG. 1 (Drucker and Lyndon, 2000).

A kinase inhibitor, STI-571 (4-[(4-methyl-piperazinyl)methyl]-N-[4-methyl-3-[[4-(3-pyrodnyl)-2-pyrimidinyl]amin]phenyl]benzamide methanesul-fonate; Glivec®, Novartis, Basel, Switzerland) was initially identified in a screen for inhibitors of the platelet derived growth factor receptor (PDGFR) (Buchdunger et al., 1995). This ATP analog of the class 2-phenylaminopyrimidine, was found to have some selectivity for specific kinases including cdc2/cyclin B, c-FGR, protein kinase C γ and v-Abl. As the constitutive activation of v-Abl is believed to be sufficient for the development of CML, it was seen as an ideal target for validating the clinical utility of protein kinase inhibitors in the treatment of cancer.

The Abl oncogene was isolated originally from the genome of the Abelson murine leukemia virus (A-MuLV) (Rosenberg and Witte, 1988). This acutely transforming replication-defective virus encodes a transforming protein (p160v-Abl) with tyrosine-specific protein kinase activity. A-MuLV transforms fibroblasts in vitro and lymphoid cells in vitro and in vivo and was formed by recombination between Moloney murine leukemia virus (M-MuLV) and the murine c-Abl gene (Rosenberg and Witte, 1988).

As with many of the viral oncogenes, there are cellular equivalents that are involved in growth and differentiation. c-Abl is expressed normally in cells where it shuttles between the cytoplasm and the nucleus. This shuttling is driven by its three nuclear localization sequences (NLS) and one nuclear export sequence (NES). The NES is located in the C-terminus of c-Abl and contains a characteristic leucine rich motif. Mutation of a single leucine (L1064A) is sufficient to disrupt the function of the NES and result in the nuclear localization of c-Abl (Taagepera et al., 1998). Alternatively, the export of wild type c-Abl from the nucleus may be inhibited by the drug leptomycin B (LMB; NSC-364372D; PD114,720; elactocin), which functions by inactivating the nuclear export mediator CRM-1/exportin-1. The inactivation of the CRM-1 is irreversible and export is arrested until new protein is synthesized.

Cell adhesion and intracellular localization of c-Abl control the kinetics of its activation. c-Abl kinase activity is dependent on integrin mediated cell adhesion (Lewis et al, 1996). Upon cell adhesion, the cytoplasmic pool of c-Abl is reactivated within 5 minutes; however, the nuclear pool of c-Abl does not become reactivated for about 30 minutes, suggesting that activation occurs in the cytoplasm and the activated protein is translocated into the nucleus. In quiescent and $G_1$ cells, nuclear c-Abl is kept in an inactive state by the nuclear retinoblastoma protein (RB) that binds to the c-Abl tyrosine kinase domain and inhibits its activity. Phosphorylation of RB by the cyclin dependent kinases (CDKs) at the $G_1/S$ boundary disrupts the RB-c-Abl complex, leading to activation of the c-Abl kinase. Nuclear c-Abl is part of the RB-E2F complex; thus, the $G_1/S$ activation of c-Abl likely contributes to the regulation of genes involved in S-phase entry.

The nuclear c-Abl can be activated by DNA damage (Baskaran et al., 1997) to induce the p73 protein, which is a functional homolog of the tumor suppressor p53 (Gong, et al., 1999; Jost et al., 1997; Wang, 2000). Overexpression of p73 can activate the transcription of p53-responsive genes and inhibit cell growth in a p53-like manner by inducing apoptosis (Jost et al., 1997). Unlike c-Abl, Bcr-Abl is constitutively activated and is localized almost exclusively to the cytoplasm. The Bcr-Abl kinase activates a number of signal transduction pathways involved in cell proliferation and apoptosis (Warmuth, M., et al. 1999). For example, Bcr-Abl, which is typically cytoplasmic, can abrogate the dependence on interleukin-3 in hematopoietic cell lines (Daley et al., 1992) and the dependence on adhesion in fibroblastic cells (Renshaw et al., 1995). In addition, cytoplasmic Bcr-Abl can inhibit apoptosis through the activation of PI3-kinase, Akt and other mechanisms (Skorski et al., 1997; Amarante-Mendes et al., 1998). This mislocalization may be essential to the pathology of the protein.

STI 571 was shown to suppress the proliferation of Bcr-Abl-expressing cells in vitro and in vivo (Jost et al., 1999). In colony-forming assays of peripheral blood or bone marrow from patients with CML, STI 571 caused a 92–98% decrease in the number of Bcr-Abl colonies formed, with minimal inhibition of normal colony formation. (Jost et al., 1999) However, continual suppression of the Bcr-Abl tyrosine kinase is required for maximal clinical benefit in CML. Early studies demonstrated that Bcr-Abl-expressing cells could be rescued from apoptotic cell death if STI 571 were washed out of the cells within 16 hours of initial exposure (Drucker et al., 1996). If a tyrosine kinase inhibitor inhibited proliferation of Bcr-Abl-positive cells without inducing cell death, then long-term therapy would likely be required, suggesting that a well-tolerated, oral formulation of the drug would be needed.

Early pharmacokinetic studies in rats and dogs demonstrated that bioactive concentrations of STI571 are readily achieved in the circulation. However, the half-life of the drug is relatively short, 12–14 hours. In vivo STI571 treatment of nude mice injected with human leukemic cells was shown to eradicate 70–100% of the tumors. However, maintenance of a sufficiently high level of drug was essential for effective treatment. Mice receiving drug one or two times per day did not show significant improvements, whereas the mice receiving drug three times per day greatly improved (le Coutre et al., 1999). Additionally, relapse was seen in some animals which seemed to be mainly dependent on initial tumor load.

These pharmacokinetic properties make the drug less desirable for long term use. If a patient must take the drug long term, the chances of a patient maintaining a strict regimen of taking the drug on a strict interval decrease. No maximum tolerated dose has been identified for STI571 (Drucker, 2001a); however, its side effects are non-trivial for a drug that one must take in a regimented manner for an indefinite period of time. The most common side effects include nausea (in 43 percent of patients), myalgias (41 percent), edema (39 percent) and diarrhea (25 percent). Other side effects included fatigue, rash, dyspepsia, vomiting, theormbocytopenia, neutropenia and arthralgias.

Fluctuations in drug levels allow for the development of drug resistance which has been shown to happen in tissue culture (le Coutre et a., 2000). Treatment of LAMA84 human bcr-abl cells in culture with an initially sub-lethal, but continuously increasing dose of STI571 resulted in the development of a resistant cell line that was ten-fold more resistant to STI571 as compared to the parental cell line. Effectively, the process would be mimicked in a patient that did not adhere to a proper drug regimen. The cancer cells would be exposed to an insufficient dose of drug to induce quiescence or kill the more malignant cancer cells, allowing expansion of the resistant cells. Resistance develops by the amplification of the bcr-abl gene, a process which occurs during the blast crisis of the disease. Lack of adherence to the proper dosing regimen could hasten the onset of the blast crisis stage of the disease by promoting amplification of the gene.

Patients not responsive to standard interferon-α therapy were enrolled on a study to test the efficacy of STI571 as a chemotherapeutic agent (Drucker et al., 2001a). The study demonstrated that a relatively high level of drug must be maintained to have a therapeutic effect. Responses to STI571 were evaluated in two ways, hematologic, with complete response defined as a white-cell count of less than 10,000 per cubic millimeter; and cytogenetic, with a major response defined as less than 35 percent of the 20 metaphase cells analyzed positive for the Philadelphia chromosome. Hematologic responses were seen within two weeks, and all but one patient treated with 300 mg or more per day showed complete hematological response within four weeks. Only 31 percent of the patients had major cytogenetic responses, including 7 percent that showed complete cytogenetic remission. Cytogenetic responses occurred as early as two months and as late as 10 months. However, blood counts were maintained within normal limits regardless of whether a cytogenetic response was observed. Additionally, during treatment with STI571, blood counts gradually returned to normal during the first month, suggesting that the drug does not rapidly induce apoptosis, as would be expected with standard chemotherapy. Therefore, the drug seems to act by holding the diseased cells in abeyance rather than by killing them. This further emphasizes the need to maintain patients on STI571 indefinitely.

STI571 was also tested for efficacy in the treatment of patients who had entered the blast crisis of CML and acute lymphoblastic leukemia (ALL) (Drucker et al., 2001b). The blast crisis is highly refractory to treatment. The rate of response to standard induction chemotherapy is approximately 20 percent in myeloid blast crisis and 50 percent in lymphoid blast crisis. However, the remission seen is typically short lived. The blast crisis phase of both diseases is associated with genetic instability and multiple genetic abnormalities. Of the 58 patients enrolled in the study, 16 died due to disease progression. Other serious adverse events included nausea and vomiting, febrile neutropenia, elevated liver enzyme levels, exfoliative dermatitis, gastric hemorrage, renal failure, pancytopenia and congestive heart failure. The improvements seen in some of the patients were short lived. Of the 38 patients with myeloid blast crisis, 4 had complete hematologic remission and 17 had a decrease in blasts in the marrow to less than 15 percent. Of these 21 that showed improvement, 9 subsequently relapsed between 42 and 194 days (median 84), 7 remained in remission with a follow-up of 101 to 349 days and three discontinued the study due to adverse events. Of the 14 patients with lymphoid blast crisis who had a response to STI571, 12 relapsed between 42 and 123 days (median 58). One patient remained in remission for 243 days of follow-up. The authors of the study stated that although Bcr-Abl plays a role in the blast crisis, inhibition of the single protein alone is insufficient to treat the disease and that combination with a second agent is required.

SUMMARY OF THE INVENTION

The invention is a method for the treatment of cancers expressing the bcr-abl oncogene product by localizing an active Bcr-Abl to the nucleus to induce apoptosis. Endogenous Bcr-Abl may be accumulated in the nucleus by use of drugs that alter the localization of the protein in the cancer cell by administration of a Bcr-Abl kinase inhibitor (e.g. STI571; PD173955 or PD180970 both from Parke-Davis) and leptomycin B (LMB) (Schaumberg et al., 1984). The kinase inhibitor encourages Bcr-Abl translocation into the nucleus. Functional block of the protien is reversed by clearance or breakdown of the kinase inhibitor while the nuclear localization of the protein is maintained by LMB. Upon reactivation of the nuclear pool of Bcr-Abl, apoptosis is induced. Such a therapeutic protocol can be used in vivo for the treatment of leukemias or ex vivo to purge bone marrow to allow for autologous bone marrow transplantation.

Alternatively the coding sequence for a mutant form of bcr-abl lacking a functional nuclear export signal (NES) (SEQ ID NO 1, 2) (Taagepera et al., 1998) can be transferred into a solid tumor by use of a nucleic acid expression cassette. Methods of transfer of "suicide genes" to solid tumors followed by treatment with drugs to kill the tumor cells is known to those skilled in the art (see U.S. Pat. No. 6,066,624, incorporated herein by reference). A number of gene transfer methods are known including, but are not limited to, adenoviral viral vectors, (e.g. U.S. Pat. No. 6,080,578, incorporated herein by reference), adenovirus associated vectors (e.g. U.S. Pat. No. 5,989,540, incorporated herein by reference) or retroviral vectors (e.g. U.S. Pat. No. 6,051,427, incorporated herein by reference). Alternatively, nucleic acid can be delivered by direct injection of DNA into tumor either alone or encapsulated in liposomes or other DNA transfer reagent (e.g. U.S. Pat. No. 5,976,567, incorporated herein by reference). Translocation of the NES-defective Bcr-Abl to the nucleus is driven by administration of a kinase inhibitor. Apoptosis is promoted in cells containing the nuclear localized Bcr-Abl by washout of the kinase inhibitor to allow for activation of the protein. The rapid clearance of STI571 allows for the activation of the nuclear Bcr-Abl which induces apoptosis.

In another embodiment, the coding sequence for the NES-defective Bcr-Abl is fused in frame to the coding sequence of at least one heterologous nuclear localization signal (NLS) (e.g. SV40 large T antigen, nucleoplasmin) for transfer into a solid tumor by any of the methods listed above. The presence of the NLS abrogates the need for therapy with a kinase inhibitor or LMB. Upon translation of the protein, it is translocated into the nucleus where it activates apoptotic pathways.

This method overcomes a number of the problems with the use of STI571 as a single chemotherapeutic agent. First, the cancer cells are killed and not simply maintained in a quiescent state. This overcomes difficulties of maintaining rigorous therapeutic schedules for indefinite periods of time, increasing the quality of life for patients as well as decreasing the chances of the development of resistance. Such a therapy can be useful in blast crisis as only a portion of the Bcr-Abl must be translocated into the nucleus to induce apoptosis. The severe adverse events seen in the study with patients in the blast crisis stage of the disease would not likely be seen with less than a week of drug treatment. Steady state blood levels of 1 µM STI571 and 10 nm LMB, effective doses of the drugs in culture, can be reached in two to three days. STI571 is rapidly cleared in a predictable manner with the time line dependent on the amount of drug given to the patient. If the Bcr-Abl is the endogenous protein from the cell, the patient is maintained on LMB for 2 to 3 days after combined treatment with a kinase inhibitor and LMB to retain the protein in the nucleus. Similar time considerations would be appropriate for LMB to purge bone marrow ex vivo. Ex vivo, effective doses of kinase inhibitor and LMB can be reached essentially instantaneously. In mouse bone marrow, clearance of at least 98% of the Bcr-Abl expressing bone marrow cells was acheived by treament of the cells for 12 hours with STI571 with LMB added for the last 8 hours of STI571 treatment. Maintaining the cells in LMB alone for an additional period of time after treatment with the drugs together can increase the rate of cell killing as with the tissue culture cells. If the Bcr-Abl is a nuclear export defective mutant transferred to the tumor by gene therapy, the patient is treated with kinase inhibitor alone for up to a week to encourage the entry of the protein into the nucleus. If an NLS supplemented NES-defective Bcr-Abl construct is used, no treatment with drugs is required. Upon completion of the first round of chemotherapy, the patient is monitored and the regimen may be repeated as needed.

BRIEF DESCRIPTION OF THE DRAWINGS

FIG. 1. Table of selected small molecule ATP-competitive protein kinase inhibitors in development.

FIG. 2. Nuclear localization of active Bcr-Abl kinase kills cells.

The present invention will be better understood from the following detailed description of an exemplary embodiment of the invention, taken in conjunction with the accompanying drawings in which like reference numerals refer to like parts and in which:

DETAILED DESCRIPTION AND PREFERRED EMBODIMENTS

Figure 3:
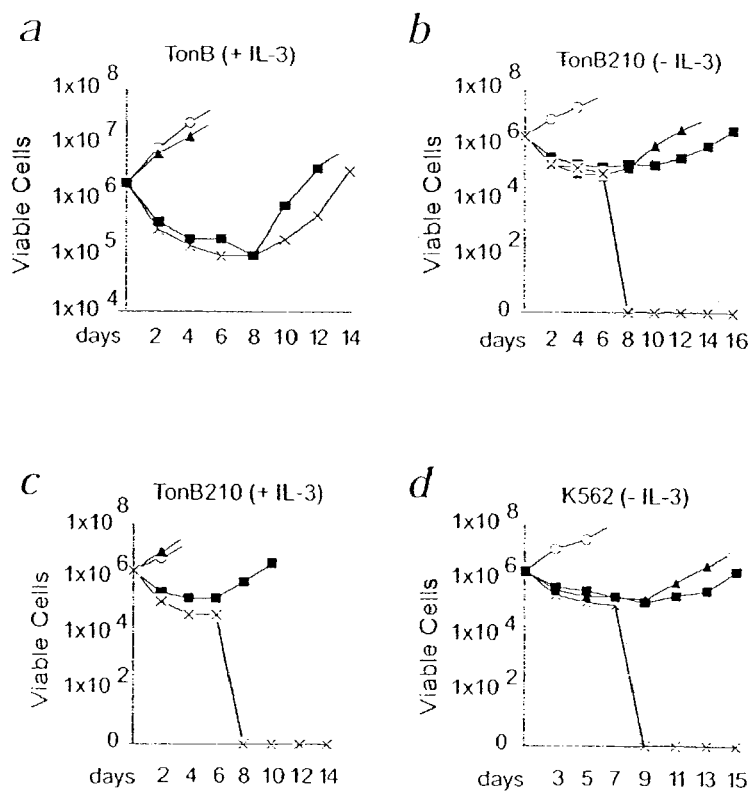
FIG. 3. Irreversible killing of Bcr-Abl transformed cells. The indicated cells were left untreated (○), exposed to LMB (■), STI571 (▲), or to both drugs (x) for 48 hours (Ton B) or 72 hours (K562). Cells were then washed, plated in fresh media, and viable cells were counted every two days. The results of one representative experiment from three independent experiments is shown. a, Ton B cells that are not induced to express Bcr-Abl. b, TonB210 cells cultivated in the absence of IL-3. c, TonB210 cells grown in the presence of IL-3. d, K562 cells.

The cytoplasmic Bcr-Abl tyrosine kinase is a potent inhibitor of apoptosis (McGahon et al., 1994). The anti-apoptotic activity of Bcr-Abl contributes to the development of CML and the resistance of CML cells to chemotherapy (Warmuth et al., 1999). Evidence is presented that the Bcr-Abl tyrosine kinase can be converted into an activator of apoptosis by allowing it to function inside the nucleus. Apoptosis induced by the nuclear Bcr-Abl cannot be suppressed by the cytoplasmic Bcr-Abl, because nuclear entrapment of a fraction of the total Bcr-Abl is sufficient to kill cells. Because the nuclear Bcr-Abl can kill cells, cytoplasmic retention of this activated tyrosine kinase is required for cell transformation. That the Bcr-Abl kinase can induce apoptosis from the nucleus is consistent with the role of the nuclear c-Abl tyrosine kinase in the activation of cell death (Gong et al., 1999; Wang, 2000).

The discovery of STI571 has raised the prospect of a CML treatment with increased efficacy and limited side effects (Drucker and Lyndon, 2000). STI571 has shown efficacy in phase I and phase 11 clinical trials on CML patients in the chronic phase (Goldman, 2000). It is already evident, however, that STI571 does not have a long-term efficacy on CML patients in the acute phase (Vastag, 2000). Moreover, prolonged exposure to STI571, CML cells could develop resistance to this drug (Gambacourti, et al., 2000; le Coutre et al., 2000; Mahon et al., 2000; Weisberg and Griffin, 2000). LMB is a potent inhibitor of cell proliferation; however, its therapeutic application is limited by neuronal toxicity observed in a phase I clinical trial (Newlands et al., 1996). Though LMB is toxic to cells irrespective of Bcr-Abl expression, its effect is reversible after drug removal. Experiments on mouse bone marrow cells suggest that the combined treatment with LMB and STI571 is useful to purge explanted bone marrow of CML cells. This purging strategy allows autologous bone marrow transplantation to become a therapeutic option for CML.

Previous studies have shown that STI571 could induce apoptosis of CML cell lines in culture (Beran et al., 1998; Deininger et al., 1997). Herein is disclosed an alternative mechanism to induce apoptosis through STI571. When STI571 is combined with an inhibitor of nuclear export, it causes Bcr-Abl to be trapped in the nucleus. When the nuclear Bcr-Abl recovers its kinase activity, through the removal or metabolic decay of STI571, apoptosis is activated. These results indicate an interesting approach to treating CML, by trapping Bcr-Abl in the nucleus of leukemic cells and thus converting Bcr-Abl into a terminator of this disease.

Studies demonstrated that the kinase defective Bcr-Abl (Bcr-Abl-KD) entered the nucleus spontaneously; therefore, STI571 was tested to determine if it could stimulate the nuclear import of wild-type Bcr-Abl through inactivation of the kinase. $Abl^{-/-}$ fibroblast were transfected using the calcium phosphate method, well known to those skilled in the art, with plasmids encoding Bcr-Abl. Cells were treated with STI571 alone or with a combination of STI571 and LMB. Treatment with STI571 alone did not result in the nuclear accumulation of Bcr-Abl. However, the combined treatment with STI571 and LMB led to the accumulation of Bcr-Abl in the nucleus.

To quantify the stimulatory effect of STI571 on the nuclear import of Bcr-Abl without the influence of LMB, the NES of Bcr-Abl was inactivated by mutating a critical leucine residue (L1064A) (SEQ ID NO 1, 2) (Taagepera, et al., 1998). The NES mutation affects neither the kinase activity nor the interaction of Bcr-Abl with STI571, which binds to the tyrosine kinase domain (Schindler et al., 2000). When expressed in $Abl^{-/-}$ cells, BCR-Abl-NES was localized to the cytoplasm (FIG. 2a). Following incubation with STI571, BCR-Abl-NES became detectable in the nucleus (FIG. 2b). STI571 did not alter the steady-state levels of BCR-Abl-NES (FIG. 2c). The fraction of BCR-Abl-NES found in the nucleus was dependent on the concentration of STI571 and increased with time (FIG. 2d). The amount of BCR-Abl-NES in the nucleus was 5, 10 and 20%, respectively, after a 12-hour incubation with 0.1, 1 and 10 M of STI571. Between 12 and 18 hours, the amount of nuclear Bcr-Abl-NES continued to increase with 0.1 and 1 µM of STI571, but approached a plateau with 10 µM of STI571 (FIG. 2d). The in vivo $IC_{50}$ for the inhibition of Bcr-Abl tyrosine kinase is 0.25–0.4 µM (Drucker et al., 1996). Thus, the nuclear accumulation of Bcr-Abl-NES could be correlated with the inhibition of its kinase activity. The nuclear fraction of Bcr-Abl-NES at 24 hours of treatment was between 25–35%. The nuclear fraction of Bcr-Abl-KD treated with LMB alone, or Bcr-Abl treated with both LMB and STI571 was also between 25–35%. These results indicate that mechanisms other than the kinase activity also mediate the cytoplasmic retention of Bcr-Abl.

It is known that activation of the nuclear Abl tyrosine kinase by DNA damage can contribute to the induction of apoptosis (Gong et al., 1999; Wang, 2000). Similarly, when translocated into the nucleus, Bcr-Abl kinase can activate apoptosis. The mere expression of Bcr-Abl does not cause apoptosis (as measured by TUNEL assay). However, trapping Bcr-Abl in the nucleus by combined treatment with STI571 and LMB caused apoptosis in 20% of Bcr-Abl expressing cells, which was not significantly different from the 10% of untransfected cells (Table 2). Maintenance of Bcr-Abl in the inactivated form did not stimulate apoptosis. However, removal of the inhibitor while maintaining the Bcr-Abl in the nucleus strongly stimulated apoptosis. Following incubation with both STI571 and LMB to trap Bcr-Abl in the nucleus, cells were washed extensively and placed in fresh media with LMB alone to allow the recovery of Bcr-Abl kinase activity in the nucleus. With this protocol, between 70–80% of the Bcr-Abl expressing cells were positive for TUNEL staining, whereas the apoptosis rate remained at the 10% level with untransfected cells (Table 2). By expressing Bcr-Abl-KD and treating cells with LMB alone, it was confirmed that an active nuclear Bcr-Abl kinase was required to induce apoptosis. Despite its nuclear accumulation, Bcr-Abl-KD did not induce apoptosis (Table 2).

The inhibition of nuclear export by LMB has a cytotoxic effect of its own. To rule out that Bcr-Abl-induced apoptosis is dependent entirely on LMB, BCR-Abl-NES, which could be trapped in the nucleus by treatment with STI571 alone was tested for its ability to induce apoptosis (Table 2). The nuclear accumulation and re-activation of BCR-Abl-NES was able to cause apoptosis, in that 60% of the BCR-Abl-NES expressing cells became TUNEL-positive as compared with only 3% of the untransfected cells (Table 2). This result demonstrates that the nuclear Bcr-Abl kinase induces apoptosis in the absence of LMB.

Response to the drug regimen was further tested in a CML cell line, K562, and a non-CML myeloid leukemic cell line, HL60. Treatment of cells with a combination of STI571 and LMB for 8 hours, followed by treatment of the cells with LMB alone for 4 hours induced apoptosis in the K562 cells, but not in the HL60 cell line, further confirming the role of Bcr-Abl in the killing of the cells. Additionally, the studies demonstrated that the constitutively expressed Bcr-Abl, rather than just transiently expressed Bcr-Abl, may participate in the cell killing process induced by STI571 and LMB.

STI571 is more effective in preventing cells from dividing than it is in killing them. Upon removal of the drug, cells are able to proliferate again. To determine the efficacy and the specificity of cell killing by the nuclear Bcr-Abl, the long-term survival of drug-treated cells was investigated. The murine pro-B cell line TonB, which can be induced to express p210 Bcr-Abl through a doxycycline-regulated promoter was used (Klucher et al., 1998). The uninduced TonB and the induced TonB210 (expressing Bcr-Abl) cells were treated for a total of 48 hours with either LMB or STI571 alone, or both drugs combined. At the end of the 48-hour period, cells were washed extensively, placed in fresh media and the number of live cells was counted every 48 hours for a total of 14 to 16 days (FIGS. 3a–c).

TonB cells that were not induced to express Bcr-Abl did not exhibit any reaction to STI571 (FIG. 3a). Treatment of TonB cells with LMB alone or with LMB plus STI571 caused a reduction in cell numbers (FIG. 3a). LMB causes an irreversible inactivation of Crm1/exportin-1 (Kudo et al., 1999); however, cells can recover from LMB, through the de novo synthesis of Crm1/exportin-1. Indeed, TonB cells resumed growth several days after the removal of LMB (compare FIG. 3a). Because TonB cells are dependent on IL-3 for survival and proliferation (Klucher et al., 1998), IL-3 was included in these experiments.

TonB210 cells induced to express Bcr-Abl became IL-3-independent (Klucher et al., 1998). The drug treatments were performed on TonB210 cells with and without IL-3. Without IL-3, TonB210 cells were sensitive to treatment with STI571 (FIG. 3b). Treatment with LMB alone for 48 hours also caused a decrease in cell numbers. Nevertheless, TonB210 cells could resume growth following the removal of LMB or STI571 (FIG. 3b). In contrast, the combined treatment with STI571 and LMB for 48 hours caused the complete loss of viable cells after the removal of drugs (FIG. 3b). With IL-3, TonB210 cells were not sensitive to treatment with STI571 (FIG. 3c). The inclusion of IL-3 also promoted the recovery of TonB210 cells following the removal of LMB (compare FIGS. 3b and c). However, even with the continuous presence of IL-3, treatment with a combination of STI571 and LMB caused a complete eradication of the TonB210 population following drug removal (FIG. 3c). In combination with LMB, concentrations of STI571 between 1 to 10 μM were similarly effective in mediating the complete killing of TonB210.

Irreversible killing by the combined action of STI571 and LMB in the blast crisis cell line K562 was observed (FIG. 3d). Similar to the murine TonB210 cells, K562 cells showed initial death when STI571 was present, but this was consistently followed by recovery after the removal of STI571 (FIG. 3d). A similar initial decline in cell number was observed and recovery when K562 cells were treated with LMB alone (FIG. 3d). Again, treatment with both STI571 and LMB resulted in the complete loss of viable K562 cells by six days after drug removal.

The precipitous decline in viable TonB210 or K562 cells occurred several days after the removal of both drugs (FIGS. 3b–d). One reason for this delayed killing could be the time required to recover the Bcr-Abl kinase activity in the nucleus. The tyrosine-phosphorylated proteins in total cell lysates were examined at the end of drug treatments and then before their precipitous death. TonB cells showed a low level of tyrosine phosphorylation, which was not affected by the drug treatments. In TonB210 and K562 cells, the overall levels of tyrosine-phosphorylated proteins decreased following incubation with STI571 alone or STI571 plus LMB. Before cell death, the levels of tyrosine phosphorylation returned to those of untreated cells. Thus, the precipitous death could be correlated with the recovery of Bcr-Abl kinase activity.

Figure 4:
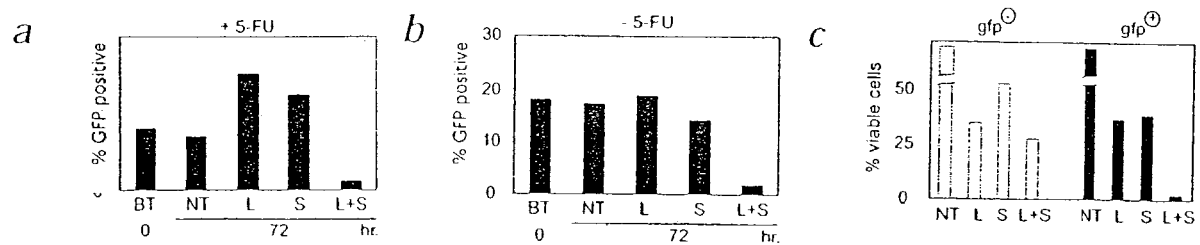
FIG. 4. Preferential killing of mouse bone marrow cells expressing Bcr-Abl. a, Murine bone marrow cells were collected 5 days after 5-FU injection. Cells were infected with MSCV-Bcr-Abl/P210-IRES-GFP retrovirus. A mixed population of infected and uninfected cells was analyzed by FACS to determine the percentage of GFP$^+$ cells before treatment (BT). The population was divided equally among 4 conditions: untreated (NT), incubated with LMB (L), STI571 (S), or STI571 plus LMB (S+L). After drug removal, cells were cultured in normal growth media and the collected for FACS analysis. The results shown are from a representative experiment performed in duplicate. b, The same experiment as in a was repeated with bone marrow cells from mice that were not injected with 5-FU. c, Total number of live cells from experiment in b were determined and normalized to the cell number of the mixed population before treatment. The unifected (GFP$^-$) and the infected (GFP$^+$) cells were similarly sensitive to treatment with LMB or STI alone. The GFP$^+$ cells were extremely sensitive to the combined treatment, whereas the GFP$^-$ cells were not.

Recent studies have shown that infection of mouse bone marrow cells with a Bcr-Abl retrovirus can cause a CML-like syndrome following transplantation of infected cells into syngeneic mice (Daley et al., 1990; Li et al., 1999; Pear et al., 1998; Zhang et al., 1998). As an ex vivo verification of the results obtained with cell lines, STI571 and LMB were tested for their ability to kill Bcr-Abl-infected primary bone marrow cells. Mouse bone marrow cells were collected 5 days after 5-fluoracil (5-FU) injection. Cells were infected with a retrovirus that expresses the p210 Bcr-Abl and the green fluorescent protein (GFP) from a single bi-cistronic RNA (Zhang et al., 1998). The Bcr-Abl-infected cells could therefore be followed as GFP$^+$ cells. Mixed populations of GFP$^+$ and GFP$^-$ bone marrow cells were treated with STI and LMB either alone or in combination for a total of 12 hours, washed and cultured the cells for 60 hours. The percentage of GFP$^+$ cells were determined by FACS (FIG. 4). Before treatment (BT), 10–12% of the population was positive for GFP. In the untreated populations (NT), the GFP$^+$ cells remained at 10–12%. Treatment with LMB (L) or STI571 (S) alone resulted in a moderate increase in the percent of GFP$^+$ cells. However, the combined treatment with LMB and STI571 (L+S) reduced the GFP$^+$ cells to a level of 1–2%. These experiments demonstrate that the treatment regimen is useful for the killing of Bcr-Abl cells ex vivo as well as in vitro.

A similar experiment was performed with bone marrow cells isolated from mice that had not been injected with 5-FU (FIG. 4b). Before treatment, 18–20% of the cells were positive for GFP (BT). Treatment with LMB or STI571 alone had no significant effect on the percentage of GFP$^+$ cells (FIG. 4b). The combined treatment with LMB and STI571 again reduced the GFP$^+$ cells to 1–2% (FIG. 4b). The total number of GFP$^-$ and GFP$^+$ cells were determined in these populations (FIG. 4c). Without drug treatment, both GFP$^-$ and GFP$^+$ cells increased by 40–50% relative to the starting populations (FIG. 4c, NT). LMB exhibited a toxic effect by reducing both the GFP$^-$ and GFP$^+$ cells to a similar level (FIG. 4c, L). STI571 was also toxic to both the GFP$^-$ and GFP$^+$ cells (FIG. 4c, S). The mouse bone marrow cells were cultured in media containing the stem-cell factor, which acts through the c-Kit receptor tyrosine kinase. Because STI571 can inhibit the c-Kit tyrosine kinase (Heinrich et al., 2000), the sensitivity of GFP$^-$ cells to STI571 could be due to the interference of c-Kit function. The combined treatment with STI571 and LMB was somewhat more toxic to the GFP$^-$ cells then either drug alone (FIG. 4c). However, the combined treatment with STI571 and LMB removed the majority (>97%) of the GFP$^+$ cells (FIG. c). Thus, primary bone marrow cells that had been infected with a retrovirus to express the Bcr-Abl tyrosine kinase could be preferentially eliminated by the combined treatment with LMB and STI571.

EXAMPLE 1

Transfection and Immunoblotting. Transfection experiments were performed using the calcium phosphate method. Immunoblots were performed using 1 μg/ml 4G10 monoclonal antibody against phosphotyrosine (Upstate Biotechnology, Waltham, Mass.), or 1 μg/ml monoclonal antibody against Abl (8E9) (Pharmingen, San Diego, Calif.). All immunoblots were revealed by enhanced chemiluminescence (Amersham, Little Chalfont, UK).

EXAMPLE 2

Plasmids. The murine Abl-NES and p190 Bcr-Abl-KD have been described (Cortez et al., 1995; McWhirter and Wang, 1993; and Taagpera, et al., 1998). The BcrAbl-NES was engineered by joining the first 1527 base pairs of human Bcr with the last 3117 base pairs of murine Abl-NES.

EXAMPLE 3

Immunofluorescence. Abl$^{-/-}$ fibroblasts were seeded onto cover slips, transfected with the specified expression plasmids and fixed for immunofluorescence 48 h after transfection. The non-adherent TonB210 and K562 cells were seeded onto poly-L-lysine (Sigma) coated cover slips for 3 h and then processed for immunofluorescence. Cells were permeabilized for 10 min with 0.3% Triton X-100 (Sigma), then blocked at room temperature (RT) for 45 to 60 min with 10% normal goat serum (Gibco, Rockville, Md.), and incubated at RT with anti-Abl 8E9 (30 μg/mL) for 60 to 90 min. Cover slips were incubated at RT for 45 to 60 min with Alexa Fluor 594 goat secondary antibody against mouse (Molecular Probes, Eugene, Oreg.) and with Phalloidin-conjugated Alexa Fluor 488 (Molecular Probes) to stain for F-Actin. After DNA staining with Hoechst 33258 (Sigma), cover slips were mounted onto glass slides with gel mount (Biomeda, Foster City, Calif.). Epifluorescence microscopy was performed with a Nikon microscope and two-dimensional images were digitally acquired with a 0.60X HRD060-NIK CCD-Camera (Diagnostic Instruments, Sterling Heights, Mich.). Deconvolution microscopy was performed with a Deltavision™ System. At least 40 optical sections (0.2 microns) were collected for each cell. Quantification of nuclear signal was performed with the Image-Pro Plus 3.0 software (Media Cybernetics, Silver Spring, Md.). For each sample, 40 images in 2 dimensions and 4 images in 3 dimensions were acquired. Nuclear intensity (single pixel intensity x total number of pixels per nucleus) and cytoplasmic intensity (single pixel intensity number of pixels per cell—nuclear intensity) were calculated. Values obtained from images acquired in two dimensions (40 cells±s.d.) were corrected for cytoplasmic contamination of nuclear signal based on the parameters obtained from deconvolution microscopy.

EXAMPLE 4

Cell Death Assays. TUNEL assays were performed with the apoptosis detection system, Fluorescein (Promega) according to the manufacturer's protocol. Transfected cells were treated with STI571 alone for 12 h followed by LMB plus STI571 for another 12 h. The STI571 was then washed away and cells were kept in LMB for another 12 h to allow the recovery of Bcr-Abl kinase activity in the nucleus. TUNEL-positive cells were scored from both Bcr-Abl-expressing and untransfected cells on the same coverslip with at least 30 TUNEL-positive cells counted per experiment.

Annexin V binding to phosphatidylserine was measured with the Vybrant™ apoptosis assay kit #2 (Molecular Probes) following the manufacturer's recommendations. Cells were analyzed with a FACSCalibur (Becton Dickinson, Franklin Lakes, N.J.) flow cytometer. Caspase-3 activity was measured with the Enzchek™ caspase-3 assay kit #1 (Molecular Probes) according to the manufacturer's protocol. Fluorescence emission was then detected at 450 nM with a Spectramax Gemini Dual Scanning Microplate Spectrofluorometer (Molecular Devices, Sunnyvale, Calif.).

EXAMPLE 5

Cell Survival Assay. 2×10$^6$ TonB, TonB210 or K562 cells were plated and either left untreated or exposed to LMB, STI571, or a combination of the two drugs. After 48 h (TonB, TonB210) or 72 h (K562), live cells were counted with the Trypan blue exclusion assay. Cells were then washed extensively with PBS and placed in growth media. Trypan blue cell counts were repeated every 48 h and followed by feeding with fresh media. Cell counts were stopped when the number of viable cells was higher than the number of cells originally plated.

EXAMPLE 6

Specific killing of Bcr-Abl expressing cells in primary mouse bone marrow cells. Bone marrow was collected from mice as described (Li et al., 1991) with minor modifications. 6-wk-old Balb/c mice (Jackson, Bar Harbor, Me.) were either injected (IV) with 5-FU (5 mg) or left untreated. After 5 days, the mice were killed and their bone marrow was collected under sterile conditions. After 24 h, cells were infected with the supernatant of Bosc23 cells (Pear et al., 1993) transfected two days earlier with murine stem cell retrovirus (MSCV)-Bcr-Abl/p210-IRES-GFP (Zhang et al., 1998). Retroviral infection was carried out by cosedimentation at 1000 g for 90 min in a Sorvall RT-7 centrifuge (Sorvall, Newtown, Conn.). Medium was changed after 5 hours of adsorption and the next day the cells were subjected to a second round of retroviral transduction. The mixed GFP$^+$ and GFP$^-$ cell population was divided into 4 treatment conditions: untreated, exposed to 10 nM LMB for 8 h, 10 μM STI571 for 12 h or a combined treatment of 10 μM STI571 for 12 h period with 10 nM LMB added for the last 8 h. At the end of the 12-hour period, the cells were replated in prestimulation medium and cultured for 60 h. Cells were then collected and analyzed with a FACSCalibur fluorescent cell sorter (Becton Dickinson) to determine the number of GFP$^-$ and GFP$^+$ cells.

EXAMPLE 7

Treatment of CML with STI571-LMB combined therapy. Patients with CML in the chronic phase, defined by the presence of less than 15 percent blasts or basophils in the peripheral blood, who test positive for the Philadelphia chromosome are considered eligible for such therapy. Baseline lab values, including blood cell counts, are obtained before the initiation of therapy. Patients are treated for two to four days with a combination of STI571 at a dose of 500–1000 μg per day, administered orally, and LMB at a dose of 50–2000 μg per day administered inraveneously. After the initial treatment with both drugs, administration of STI571 is discontinued. Administration of LMB is continued for 3–5 days at the same or reduced level. Approximately one week after the course of treatment is completed, laboratory values are again obtained to determine the efficacy of treatment. The regimen is repeated as required at 1 to 3 month intervals until disease is eradicated.

EXAMPLE 8

Treatment of patients in blast crisis phase of CML. Treatment regimens of patients in blast crisis phase of CML is essentially identical to the treatment method of patients in the chronic phase. As only a portion of the cellular Bcr-Abl needs to be translocated into the nucleus for the therapy to work, higher doses of the drugs should not be required. Patients are treated concurrently with the two drugs for 2 to 4 days, followed by treatment with LMB alone for 3–5 days. Efficacy of the course of treatment is evaluated approximately one week after it is completed. The regimen may be repeated and/or combined with purging of bone marrow ex vivo as described in Example 11.

EXAMPLE 9

Treatment of solid tumors with gene transfer of NES-defective Bcr-Abl and STI571-LMB combined therapy. Bcr-Abl does not induce the formation of solid tumors; therefore, therapy comprising administration of 300–1000 µg/day of STI571 and LMB would not be useful in the treatment of such tumors. However, the introduction of "suicide genes" into tumors to cause them to become susceptible to drug treatments. The adenoviral E1B mutated vector of U.S. Pat. No. 6,080,578 can readily be modified to express a nuclear export defective Bcr-Abl. The adenovirus is injected into the tumor. Two to five days after injection, the patient is treated with a combination of STI571 (300–1000 µg per day) and LMB (50–2000 µg per day) for 2 to 4 days. As the Bcr-Abl does not contain a functional nuclear export signal, it is not necessary to maintain the patient on LMB after the initial administration of the LMB. Approximately a week after treatment, the patient is monitored for changes in tumor size and other properties.

EXAMPLE 10

Treatment of solid tumors with a nuclear targeted Bcr-Abl. A modified brc-abl construct has been generated that contains a mutated nuclear export signal and three SV40 large T antigen nuclear localization signals (SEQ ID NO 3, 4). The modified Bcr-Abl protein localizes to the nucleus in the absence of drug. An adenoviral associated vector carrying the coding sequence for this protein is injected directly into solid tumors. The protein is expressed in the nucleus and induces apoptosis killing the cancer cells in the tumor.

EXAMPLE 11

Autologous bone marrow transplant for the treatment of CML. Bone marrow is extracted from a patient with CML and transferred into culture ex vivo. Cells are purged of Bcr-Abl expressing cells by treatment with a kinase inhibitor and a nuclear export inhibitor together, followed by treatment with the nuclear export inhibitor alone. Cells are treated with a combination of a final concentration of 0.01–50 µM, preferably 1 µM, STI571 and 0.1–500 nM, preferably 10 nM LMB for 8 to 48 hours, preferably 12 hours, with LMB alone added for the last 4–48 hours, preferably 12 hours. Purged cells are then washed, possibly expanded, and prepared for transfusion back into the patient. During the time that the bone marrow cells are being purged, the patient is treated with full body radiation to kill the leukemic cells. Subsequently the purged bone marrow is returned to the patient and the disease state is monitored.

REFERENCES

Amarante-Mendes, G. P. et al. (1998) Bcr-Abl exerts its antiapoptotic effect against diverse apoptotic stimuli through blockage of mitochondrial release of cytochrome C and activation of caspase-3. *Blood* 91:1700–1705.

Bartram, C. R. et al. (1983) Translocation of c-abl correlates with the presence of a Philadelphia chromosome in chronic myelocytic leukemia. *Nature.* 306:277–280.

Baskaran, R., Wood, L. D., Whitaker, L. L., Canman, C. E., Morgan, S. E., Xu, Y., Barlow, C., Baltimore, D., Wynshaw-Boris, A., Kastan, M. B., Wang, J. Y. (1997) Ataxia telangiectasia mutant protein activates c-Abl tyrosine kinase in response to ionizing radiation. *Nature.* 387:516–9

Ben-Neriah, Y., Daley, G. Q., Mes-Masson, A. -M., Witte, O. N., and Baltimore, D. (1986) The chronic myelogenous leukemia-specific P210 protein is the product of the bcr/abl hybrid gene. *Science.* 233:212–214.

Beran, M. et al. (1998) Selective inhibition of cell proliferation and BCR-ABL phosphorylation in acute lymphoblastic leukemia cells expressing $M_r$ 190,000 BCR-ABL protein by a tyrosine kinase inhibitor (CGP-57148). *Clin. Cancer Res.* 4, 1661–1672.

Buchdunger, E. et al. (1995) Selective inhibition of the platelet-derived growth factor signal transduction pathway by a protein-tyrosine kinase inhibitor of the 2-phenylaminopyrimidine class. *Proc. Natl. Acad. Sci. USA.* 92:2558–2562.

Clark, S. S. et al.(1988) Expression of a distinctive Bcr-Abl oncogene in Ph1-positive acute lymphocytic leukemia (ALL). *Science.* 239:775–777.

Cortez, D., Kaldec, L. and Pendergast, A. M. (1995) Structural and signaling requirements for BCR-ABL-mediated transformation and inhibition of apoptosis. *Mol. Cell. Biol.* 15:5531–41.

Daley, G. Q., Van Etten, R. A., and Baltimore, D. (1990) Induction of chronic myelogenous leukemia in mice by the P210bcr/abl gene of the Philadelphia chromosome. *Science,* 247:824–830.

Daley, G. Q., Van Etten, R. A., Jackson, P. K., Bernards, A. and Baltimore, D. (1992) Nonmyristoylated Abl proteins transform a factor-dependent hematopoietic cell line. *Mol. Cell. Biol.* 12, 1864–1871.

Deininger, M. W., Goldman, J. M., Lydon, N. and Melo, J. V. (1997) The tyrosine kinase inhibitor CGP57148B selectively inhibits the growth of Bcr-Abl-positive cells. *Blood* 90, 3691–3698.

Druker, B. J. et al. (1996) Effects of a selective inhibitor of the ABL tyrosine kinase on the growth of BCR-ABL positive cells. *Nat. Med.* 2:561–566.

Drucker, B. J. and Lyndon, N. B. (2000) Lessons learned from the development of an Abl tyrosine kinase inhibitor for chronic myelogenous leukemia. *J. Clin. Invest.* 105:3–7.

Drucker, B. J. et al. (2001a) Efficacy and safety of a specific inhibitor of the bcr-abl tyrosine kinase in chronic myeloid leukemia. *N. Engl. J. Med.* 344:1031–1037.

Drucker. B. J. et al. (2001b) Activity of a specific inhibitor of the bcr-abl tyrosine kinase inhibitor in the blast crisis of chronic myeloid leukemia and acute lymphoblastic leukemia with the Philadelphia chromosome. *N. Engl. J. Med.* 344:1038–1042.

Gambacorti-Passerini, C. et al. (2000) Role of alpha1 Acid Glycoprotein in the In Vivo Resistance of Human BCR-ABL(+) Leukemic Cells to the Abl Inhibitor STI571. *J. Natl. Cancer Inst.* 92, 1641–1650.

Goldman, J. M. (2000) Tyrosine-kinase inhibition treatment of chronic myeloid leukemia. *Lancet* 355:1031–1032.

Gong, J. G. et al. (1999) The tyrosine kinase Abl regulates p73 in apoptotic response to cisplatin-induced DNA damage. *Nature.* 399:806–809.

Heinrich, M. C. et al. (2000) Inhibition of c-kit receptor tyrosine kinase activity by STI571, a selective tyrosine kinase inhibitor. *Blood* 96:925–932.

Heisterkamp, N. et al. (1983) Localization of the c-abl oncogene adjacent to a translocation break point in chronic myelocytic leukemia. *Nature.* 306:239–242.

Hermans, A. et al. (1987) Unique fusion of bcr and c-abl genes in Philadelphia chromosome positive acute lymphoblastic leukemia. *Cell.* 51:33–40.

Jost, C. A., Marin, M. C. and Kaelin, W. G., Jr. (1997) p73 is a simian [correction of human] p53-related protein that can induce apoptosis. *Nature* 389:191–194; erratum: 399: 817 (1999).

Klucher, K. M., Lopez, D. V. and Daley, G. Q. (1998) Secondary mutation maintains the transformed state in BaF3 cells with inducible BCR/ABL expression. *Blood* 91:3927–3934.

Kolibaba, K. S., and Druker, B. J. (1997) Protein tyrosine kinases and cancer. Biochim. Biophys. Acta. 1333:F217-F248.

Konopka, J. B., Watanabe, S. M., and Witte, O. N. 1984. An alteration of the human c-abl protein in K562 unmasks associated tyrosine kinase activity. *Cell.* 37:1035–1042

Kudo, N. et al. (1999) Leptomycin B inactivates CRM1/exportin 1 by covalent modification at a cysteine residue in the central conserved region. *Proc. Natl. Acad. Sci. USA* 96:9112–9117.

Kurzrock, R., Gutterman, J. U., and Talpaz, M. (1988) The molecular genetics of Philadelphia chromosome-positive leukemias. *N. Engl. J. Med.* 319:990–998.

le Coutre, P. et al. (1999) In vivo eradication of human BCR/ABL-positive leukemia cells with an ABL kinase inhibitor. *J. Natl. Cancer Inst.* 91:163–168.

le Coutre, P. et al. (2000) Induction of resistance to the Abelson inhibitor STI571 in human leukemic cells through gene amplification. *Blood* 95, 1758–1766.

Lewis, J. M., Baskaran, R., Taagepera, S., Schwartz, M. A. and Wang, J. Y. J (1996) Integrin regulation of c-Abl tyrosine kinase activity and cytoplasmic-nuclear transport. *Proc. Natl. Acad. Sci, USA* 93:15174–79.

Li, S., Ilaria, R. L. Jr, Million, R. P., Daley, G. Q. and Van Etten, R. A. (1999) The P190, P210, and P230 forms of the BCR/ABL oncogene induce a similar chronic myeloid leukemia-like syndrome in mice but have different lymphoid leukemogenic activity. *J. Exp. Med.* 189:1399–1412.

Mahon, F. X. et al. (2000) Selection and characterization of BCR-ABL positive cell lines with differential sensitivity to the tyrosine kinase inhibitor STI571: diverse mechanisms of resistance. *Blood* 96, 1070–1079.

McGahon, A. et al. (1994) BCR-ABL maintains resistance of chronic myelogenous leukemia cells to apoptotic cell death. *Blood* 83:1179–1187.

McWhirter, J. R. and Wang, J. Y. (1993) An actin-binding function contributes to transformation by the Bcr-Abl oncoprotein of Philadelphia chromosome+ human leukemias. *EMBO J.* 12:1533–1546.

Newlands, E. S., Rustin, G. J. and Brampton, M. H. (1996) Phase I trial of elactocin. *Br. J. Cancer* 74, 648–649.

Pear, W. S. et al. (1998) Efficient and rapid induction of a chronic myelogenous leukemia-like myeloproliferative disease in mice receiving P210 bcr/abl-transduced bone marrow. *Blood* 92:3780–3792.

Renshaw, M. W., McWhirter, J. R. and Wang, J. Y. (1995) The human leukemia oncogene bcr-abl abrogates the anchorage requirement but not the growth factor requirement for proliferation. *Mol. Cell. Biol.* 15, 1286–1293.

Rosenberg, N., and Witte, O. N. (1988) The viral and cellular forms of the Abelson (abl) oncogene. *Adv. Virus Res.* 35:39–81.

Rowley, J. D. (1973) A new consistent abnormality in chronic myelogenous leukaemia identified by quinacrine fluorescence and giemsa staining. *Nature.* 243:290–293.

Schaumberg, J. P., Hokanson, G. C. and French, J. C. (1984) The structures of anti-tumor antibiotics PD 114,720 and PD 114,721. *J. Chem. Soc. Chem. Commun.* 21:1450–2.

Schindler, T. et al. (2000) Structural mechanisms for STI-571 inhibition of Abelson tyrosine kinase. *Science* 289:1938–1942.

Shtivelman, E., Lifshitz, B., Gale, R. P., and Canaani, E. (1985) Fused transcript of abl and bcr genes in chronic myelogenous leukaemia. *Nature.* 315:550–554.

Skorski, T. et al. (1997) Transformation of hematopoietic cells by BCR/ABL requires activation of a PI-3k/Akt-dependent pathway. *EMBO J.* 16:6151–6161.

Taagepera, S. et al. (1998) Nuclear-cytoplasmic shuttling of ABL tyrosine kinase. *Proc. Natl. Acad. Sci., USA.* 95:7457–7462.

Vastag, B. (2000) Leukemia drug heralds molecular targeted era. *J. Natl. Cancer Inst.* 92:6–8.

Wang, J. Y. J. (2000) Regulation of cell death by the Abl tyrosine kinase. *Oncogene* 20:5643–5650.

Warmuth, M., Danhauser-Riedl, S. and Hallek, M. (1999) Molecular pathogenesis of chronic myeloid leukemia: implications for new therapeutic strategies. *Ann. Hematol.* 78:49–64.

Weisberg, E. and Griffin, J. D. (2000) Mechanism of resistance to the ABL tyrosine kinase inhibitor STI571 in BCR/ABL-transformed hematopoietic cell lines. *Blood* 95, 3498–3505.

Zhang, X. and Ren, R. (1998) Bcr-Abl efficiently induces a myeloproliferative disease and production of excess interleukin-3 and granulocyte-macrophage colony-stimulating factor in mice: a novel model for chronic myelogenous leukemia. *Blood* 92: 3829–3840.

Although an exemplary embodiment of the invention has been described above by way of example only, it will be understood by those skilled in the field that modifications may be made to the disclosed embodiment without departing from the scope of the invention, which is defined by the appended claims.

We claim:

1. A method of inducing apoptosis in leukemia cells expressing Bcr-Abl, the method comprising:
   (a) providing an in vitro cell culture comprising (i) leukemia cells expressing Bcr-Abl and (ii) a first cell culture medium;
   (b) administering to the cell culture (i) Bcr-Abl tyrosine kinase activity inhibitor STI-571, and (ii) leptomycin B (LMB), in amounts sufficient to induce accumulation of Bcr-Abl in nuclei of the leukemia cells expressing Bcr-Abl; and
   (c) replacing the cell culture medium of (b) with a second cell culture medium comprising LMB in an amount sufficient for induction of apoptosis in leukemia cells having Bcr-Abl accumulated in nuclei,
   thereby inducing apoptosis in the leukemia cells expressing Bcr-Abl.

2. A method of inducing apoptosis in leukemia cells expressing Bcr-Abl in accordance with claim 1, wherein the in vitro cell culture further comprises cells which are not leukemia cells expressing Bcr-Abl.

3. A method of inducing apoptosis in leukemia cells expressing Bcr-Abl in accordance with claim 1, wherein the leukemia cells are CML cells.

4. A method of inducing apoptosis in leukemia cells expressing Bcr-Abl in accordance with claim 1, wherein all the leukemia cells expressing Bcr-Abl are killed.

5. A method of killing bone marrow cells expressing Bcr-Abl, the method comprising:
   (a) providing an in vitro cell culture comprising (i) bone marrow cells expressing Bcr-Abl and (ii) a first cell culture medium;
   (b) administering to the cell culture (i) Bcr-Abl tyrosine kinase activity inhibitor STI-571, and (ii) leptomycin B (LMB), in amounts sufficient to induce accumulation of Bcr-Abl in nuclei of the bone marrow cells expressing Bcr-Abl; and
   (c) replacing the cell culture medium of (b) with a second cell culture medium comprising LMB in an amount sufficient for induction of apoptosis in bone marrow cells having Bcr-Abl accumulated in nuclei,
   whereby the induction of apoptosis in the bone marrow cells expressing Bcr-Abl kills the bone marrow cells expressing Bcr-Abl.

6. A method of killing bone marrow cells expressing Bcr-Abl in accordance with claim 5, wherein the in vitro cell culture further comprises cells which are not bone marrow cells expressing Bcr-Abl.

* * * * *